(12) United States Patent
Amaike et al.

(10) Patent No.: US 7,655,820 B2
(45) Date of Patent: Feb. 2, 2010

(54) METHOD FOR PRODUCING MOLECULAR COMPOUND

(75) Inventors: Masato Amaike, Ichihara (JP); Seiji Sasaoka, Takaoka (JP); Shigeru Kawamuko, Ichihara (JP); Yasuaki Hashimoto, Ninomiya (JP); Eiji Takemura, Joetsu (JP)

(73) Assignee: Nippon Soda Co., Ltd., Tokyo (JP)

( * ) Notice: Subject to any disclaimer, the term of this patent is extended or adjusted under 35 U.S.C. 154(b) by 148 days.

(21) Appl. No.: 11/850,493

(22) Filed: Sep. 5, 2007

(65) Prior Publication Data

US 2008/0058532 A1    Mar. 6, 2008

Related U.S. Application Data

(62) Division of application No. 10/432,758, filed as application No. PCT/JP01/10841 on Dec. 11, 2001, now Pat. No. 7,291,756.

(30) Foreign Application Priority Data

Dec. 11, 2000  (JP)  ............................ 2000-375528
Apr. 18, 2001  (JP)  ............................ 2001-119616

(51) Int. Cl.
*C07C 39/12*    (2006.01)
*C07C 39/16*    (2006.01)

(52) U.S. Cl. .................... 568/720; 428/402.2; 568/718

(58) Field of Classification Search .............. 428/402.2; 568/718
See application file for complete search history.

(56) References Cited

U.S. PATENT DOCUMENTS 5,346,141 A * 9/1994 Kim et al. ...................... 241/5
5,364,977 A * 11/1994 Asai et al. .................... 568/720

FOREIGN PATENT DOCUMENTS

EP    0 949 286    * 10/1999
JP    11-071449    3/1999

OTHER PUBLICATIONS

Melhan, Wu et al, "Analysis of Fat-soluble Compounds of Gouqizl by Gas Chromatography/Mass Spectrometry (GC/MS)," *Chinese Journal of Pharmaceutical Analysis*, vol. 16(6):387-389.
Chinese Office Action, Application No. 200410129976, dated Jan. 20, 2006.
The Society of Powder Technology, *Particle Design Engnieering, First Edition*, Pub. Sangyo Toshyo Ltd., Feb. 9, 1999, p. 113.
Notice for Filing Opinion, Korean Patent Application No. 10-2003-7007449.

* cited by examiner

*Primary Examiner*—Kamal A Saeed
*Assistant Examiner*—Janet L Coppins
(74) *Attorney, Agent, or Firm*—Darby & Darby PC

(57) ABSTRACT

A method for producing a molecular compound which comprises mixing and kneading a solid host compound and a solid or liquid guest compound by using a kneader and optionally followed by extruding and granulating, wherein the method further comprises one or more of the steps of holding the product at a temperature which is 50° C. or higher and not higher than the emission temperature for the guest compound, washing the formed molecular compound with a solvent capable of dissolving the guest compound, pulverizing in advance the solid host compound, and adding a poor solvent such as water prior to mixing and kneading. The method allows the production of a molecular compound having improved stability.

25 Claims, 6 Drawing Sheets

US 7,655,820 B2

METHOD FOR PRODUCING MOLECULAR COMPOUND

CROSS REFERENCE TO PRIOR APPLICATIONS

This Application is a continuation of U.S. patent application Ser. No. 10/432,758 filed May 28, 2003 which is a 371 of PCT/JP01/10841 filed Dec. 11, 2001 which claims priority of JP2000-375528 filed Dec. 11, 2000 and JP2001-119616 filed Apr. 18, 2001. All of the preceding are incorporated by reference in their entireties.

TECHNICAL FIELDS

The present invention relates to processes for the mass-production of molecular compounds having improved stability at an industrial scale. In more detail, it relates to industrial processes for the preparation of molecular compounds with improved stability by using solid-solid or solid-liquid reactions.

BACKGROUND ART

A clathrate compound has been known as one of molecular compounds that two or more compounds are bound through relatively weak interactions other than covalent bonds, represented by hydrogen bonds or van der Waals forces. The clathrate compound has a property to dissociate into the original individual constituent compounds by simple operations, and is expected to have applications to technological fields, such as selective separation of useful substances, chemical stabilization, nonvolatilization, prolongation of release and powderization, in recent years.

A variety of clathrate compounds have been reported (in patents such as Japanese Patents Laid-open Nos. Sho 61-53201, Sho 62-22701 and Hei 6-166646). Functionality of molecular compounds including clathrate compounds is decided by how individual constituent compounds assemble. Therefore, it is extremely important to control the assembling form of constituent compounds in order to produce molecular compounds.

A general method for producing molecular compounds represented by clathrate compounds is that either a host compound or a guest compound is dissolved in a solvent and a reaction is carried out in a solution. In a known method using a solvent, a molecular compound is not formed depending on the type of the solvent used, or an obtained product contains only the solvent without the guest compound or partly includes the solvent although containing the guest compound. It has been pointed out to be difficult to select conditions in some cases.

Different from the above-mentioned method, several methods have been proposed for producing molecular compounds by directly mixing a host compound with a guest compound without using a solvent. For example, Japanese Patent Laid-open No. Sho 63-35533 discloses methods that a powder host compound having a phenyl group and a hydroxyl group in a molecule and more than 12 carbons and a powder guest compound having a phenyl group and a carbonyl group in a molecule are pulverized separately and then mixed to react; that the said host compound is mixed with the aforementioned guest compound to pulverize for carrying out a reaction; and that the said host compound is mixed with the guest compound to react while pulverizing them. Methods of pulverizing and mixing in a mortar and shaking to mix by a shaker are described as actual mixing methods. Japanese Patent Laid-open No. Hei 1-213236 describes a process for the preparation of a clathrate compound in a way that a guest compound that is solid at an ordinary temperature is heated to melt, followed by an addition of a powder host compound capable of reacting with the said guest compound to form a clathrate compound. Meanwhile, kneaders and granulators have been generally used to mix food staff, to make tablets of agricultural chemicals, drugs and the like, or to modify or reinforce resins.

Every known process by a solid-solid reaction for the preparation of a molecular compound is at a small scale. Nobody has ever considered implementing the production of a molecular compound by a solid-solid reaction industrially at a large scale. Besides, no examples of applications of kneaders or granulators to solid-solid or solid-liquid reactions have been known so far. Molecular compounds with improved stability have been looked for when they are actually used as various products or materials for products.

It is an object of the present invention to provide industrial processes for the preparation of molecular compounds, particularly molecular compounds with excellent stability, by solid-solid or solid-liquid reactions.

DISCLOSURE OF THE INVENTION

In necessity of implementing industrial production of molecular compounds by solid-solid or solid-liquid reactions, the inventors studied in earnest. As a result, it was found that: a molecular compound can be mass-produced at an industrial scale in a way that a host compound is mixed and/or kneaded with a guest compound by a kneader or granulator, optionally followed by granulating; and that a molecular compound with improved stability can be produced by applying, when a molecular compound is prepared, one of the steps of holding the product for a certain period of time at a temperature of 50° C. or higher and the release temperature of the guest compound or below after a host compound is mixed and/or kneaded with a guest compound; washing the molecular compound formed by mixing and/or kneading a host compound with a guest compound with a solvent capable of dissolving the guest compound; pulverizing a solid host compound beforehand; and adding water prior to mixing and/or kneading. Thus, the present invention has been completed.

Furthermore, another find is that a clathrate compound with the target assembling form same as that formed when a solvent highly dissolving host and guest compounds is used can be produced in a way that a poor solvent dissolving a host and a guest compounds poorly is used, and further a host compound is pulverized beforehand, and preferably the product is held at above a specified temperature. Thus the present invention has been completed.

The present invention relates to a method for (1) producing a molecular compound having improved stability which comprises mixing and/or kneading a solid host compound with a solid or liquid guest compound, and characterized in that at least one of the following steps (a) to (d) is carried out: Step (a) that a host compound is mixed and/or kneaded with a guest compound and the product is held at a temperature of 50° C. or higher and the release temperature of the guest compound or lower for a fixed period of time; Step (b) that a host compound is mixed and/or kneaded with a guest compound to form a molecular compound which is then washed with a solvent capable of dissolving the guest compound; Step (c) that a solid host compound is pulverized beforehand; and Step (d) that a poor solvent which dissolves a solid host compound, solid guest compound and liquid guest compound only slightly is added prior to mixing and/or kneading. It also relates to a method (2) for producing a molecular compound according to method (1) in which the solid host compound is pulverized to an average particle size of 1.6 μm or smaller in Step (c). It also relates to a method (3) for producing a molecular compound according to methods (1) or (2) in which the solid host compound is pulverized to a particle size of 4.0 μm or smaller in Step (c). It also relates to a method (4) for producing a molecular compound according to one of methods (1) to (3) in which 80% by weight or more of the solid host compound is pulverized to 2.0 μm or smaller in particle size in Step (c). It also relates to a method (5) for producing a molecular compound according to one of methods (1) to (4) in which the pulverization in Step (c) is air jet pulverization.

The present invention also relates to a method (6) for producing a molecular compound according to one of methods (1) to (5) in which the poor solvent is added at an amount of 20 to 200% by weight to the total weight of the solid host compound and the solid or liquid guest compound prior to mixing and/or kneading in Step (d). It also relates to a method (7) for producing a molecular compound according to one of methods (1) to (6) in which the poor solvent is added, and the host compound is mixed and/or kneaded with the guest compound while heating so that the content of the solvent becomes 1% by weight or below in Step (d). It also relates to a method (8) for producing a molecular compound according to one of methods (1) to (6) in which the poor solvent is added to the host and guest compounds to mix and/or knead, followed by drying the product so that the content of the solvent is 1% by weight or less in Step (d). It also relates to a method (9) for producing a molecular compound according to one of methods (1) to (8) in which the poor solvent is added at an amount of 200 ml or more and 1000 ml or less to a mole of the solid host compound in Step (d). It also relates to a method (10) for producing a molecular compound according to one of methods (1) to (9) in which a solvent that dissolves 1 g/100 ml or less of the solid host compound, solid guest compound and liquid guest compound at room temperature is used as the poor solvent in Step (d). It also relates to a method (11) for producing a molecular compound according to one of methods (1) to (9) in which the poor solvent used in Step (d) is water.

Further, the present invention also relates to a method (12) for producing a molecular compound according to one of methods (1) to (11) in which the solid host compound is mixed with a required amount of the solid guest compound or with a necessary amount of the liquid guest compound all at once. It also relates to a method (13) for producing a molecular compound according to one of methods (1) to (12) in which a kneader is used for mixing and/or kneading. It also relates to a method (14) for producing a molecular compound in which the solid host compound is mixed and/or kneaded with the solid or liquid guest compound by a kneader. It also relates to a method (15) for producing a molecular compound according to methods (13) or (14) in which the kneader is a multi-shaft kneader. It also relates to a method (16) for producing a molecular compound according to one of methods (13) to (15) in which the solid host compound is uniformly mixed with the solid or liquid guest compound prior to mixing and/or kneading them by the kneader. It also relates to a method (17) for producing a molecular compound according to one of methods (13) to (16) in which the kneader is used for mixing and/or kneading in a temperature range where the solid host compound, guest compound and the formed molecular compound are stable. It also relates to a method (18) for producing a molecular compound according to one of methods (13) to (17) in which the solid host compound is mixed and/or kneaded with the solid or liquid guest compound by the kneader, followed by extruding and granulating.

The present invention also relates to a method (19) for producing a molecular compound in which a solid host compound pulverized to an average particle size of 1.6 μm or smaller beforehand and a solid or liquid guest compound are dispersed in a poor solvent that dissolves the solid host compound and the solid or liquid guest compound poorly.

The present invention also relates to a method (20) for producing a molecular compound in which a solid host compound pulverized to a particle size of 4.0 μm or smaller in advance and a solid or liquid guest compound are dispersed in a poor solvent that dissolves the solid host compound and solid or liquid guest compound only slightly.

The present invention also relates to a method (21) for producing a molecular compound in which 80% by weight or more of a solid host compound is pulverized to 2.0 μm or smaller in particle size beforehand in the process for the preparation of a molecular compound that a solid host compound and a solid or liquid guest compound are dispersed in a poor solvent that dissolves the solid host compound and the solid or liquid guest compound poorly.

Further, the present invention also relates to a method (22) for producing a molecular compound according to one of methods (19) to (21) in which the solid host compound is preferably pulverized by a jet stream (claim 22). It also relates to a method (23) for producing a molecular compound according to one of methods (19) to (22) in which an Ulmax pulverizer is used for the air jet pulverization of the solid host compound. It also relates to a method (24) for producing a molecular compound according to one of methods (19) to (23) in which the product is held at a temperature of 50° C. or higher and the release temperature of the guest compound or below. It also relates to a method for producing a molecular compound according to one of methods (19) to (24) in which the poor solvent is water.

The present invention also relates to a method (26) for producing a molecular compound according to one of methods (1) to (25) in which the solid host compound is 1,1,2,2-tetrakis(4-hydroxyphenyl)ethane. It also relates to a method (27) for producing a molecular compound according to one of methods (1) to (26) in which the guest compound is 2-ethyl-4-methylimidazole.

A method of the present invention for producing a molecular compound has no particular restrictions if it is (1) a method for producing a molecular compound having improved stability by mixing and/or kneading a solid host compound with a solid or liquid guest compound and applying at least one of the following steps: (a) a host compound is mixed and/or kneaded with a guest compound, and the product is held at a temperature of 50° C. or higher and the release temperature of the guest compound or below for a fixed period of time; (b) a molecular compound formed after a host compound is mixed and/or kneaded with a guest compound is washed with a solvent capable of dissolving the guest compound; (c) a solid host compound is pulverized beforehand; and (d) a poor solvent that dissolves a solid host compound, solid guest compound and liquid guest compound poorly is added prior to mixing and/or kneading; and (2) a method for mixing and/or kneading a solid host compound with a solid or liquid guest compound by a kneader. Here, a molecular compound refers to a compound that two or more constituent compounds able to exist alone and stably are bound through relatively weak interactions other than covalent bonds, represented by hydrogen bonds or van der Waals forces. Its examples includes hydrates, solvates, adducts and clathrate compounds. The said clathrate compound refers to a substance that has holes of appropriate size in the inside of three-dimensional structures formed when atoms or molecules are bound and that contains other atoms or molecules which enter into the inside of the holes by means of non-covalent bond interactions at a certain definite composition ratio. Such a molecular compound can be produced by mixing a host compound with a guest compound, and is useful in respect of having functions for selective separation, chemical stabilization, nonvolitilization and powderization of the guest compound which is a useful substance. The molecular compounds of the present invention include molecular compounds consisting of 3 or more constituents obtained by a reaction of 2 or more different types of guest compounds. The crystallinity of the molecular compound can be confirmed by examining mainly X-ray diffraction patterns. The existence of polymorphism in molecular compounds of the same composition can be checked by thermal analyses, X-ray diffraction patterns, solid-state NMR and other means.

There are no particular restrictions on solid host compounds used in the present invention if they are compounds that can take other atoms or molecules at certain definite composition ratios into holes in the inside of three-dimensional structures formed when atoms or molecules are bound so as to construct specific structures. Their actual examples include tetrakis phenols, 1,1,6,6-tetraphenyl-2,4-hexadiyn-1,6-diol, 1,6-bis(2-chlorophenyl)-1,6-diphenylhexan-2,4-diyn-1,6-diol, 1,1,4,4-tetraphenyl-2-butyn-1-1,4diol, 2,5-bis(2,4-dimethylphenyl)hydroquinone, 1,1-bis(2,4-dimethylphenyl)-2propyn-1-ol, 1,1,2,2-tetraphenylethan-1,2-diol, 1,1'-bi-2-naphthol, 9,10-diphenyl-9,10-dihydroxyanthracene, 1,1,6,6-tetra(2,4-dimethylphenyl)-2,4-hexadiyn-1,6-diol, 9,10-bis(4-methylphenyl)-9,10-dihydroxyanthracene, 1,1-bis(4-hydroxyphenyl)cyclohexane, N,N,N',N'-tetrakis(cyclohexyl)-(1,1'-biphenyl)-2,2'-dicarboxamide, 4,4'-sulfonylbisphenol, 4,4'-butylidenebis(3-methyl-6-tert-butylphenol), 2,2'-methylenbis(4-methyl-6-tert-butylphenol), 4,4'-thiobis(4-chlorophenol), 2,2'-methylenebis(4-chlorophenol), deoxycholic acid, cholic acid, α,α,α',α'-tetraphenyl-1,1'-biphenyl-2,2'dimethanol, t-butylhydroquinone, 2,5-di-tert-butylhydroquinone, granular corn starch, 1,4-diazabicyclo-(2,2,2)-octane, 3,3'-bispbenylsulfony1-4,4'-dihydroxyphenyl sulfone and tri-o-thymotide.

Actual examples of the said tetrakisphenols include tetrakis(hydroxyphenyl)alkanes such as 1,1,2,2-tetrakis(4-hydroxyphenyl)ethane (hereinafter referred to as "TEP"), 1,1,2,2-tetrakis(3-fluoro-4-hydroxyphenyl)ethane, 1,1,2,2-tetrakis(3-chloro-4-hydroxyphenyl)ethane, 1,1,2,2-tetrakis(3-methyl-4-hydroxyphenyl)ethane, 1,1,2,2tetrakis(3-methoxy-4-hydroxyphenyl)ethane, 1,1,2,2-tetrakis(3,5-dimethyl-4-hydroxyphenyl) ethane, 1,1,3,3-tetrakis(4-hydroxyphenyl)propane, 1,1,3,3-tetrakis(3-fluoro-4-hydroxyphenyl)propane, 1,1,3,3-tetrakis(3-chloro-4-hydroxyphenyl)propane, 1,1,3,3-tetrakis(3-methyl-4-hydroxyphenyl)propane, 1,1,3,3-tetrakis(3-methoxy-4-hydroxyphenyl)propane, 1,1,3,3-tetrakis(3,5-dimethyl-4-hydroxyphenyl)propane, 1,1,4,4-tetrakis(4-hydroxyphenyl)butane, 1,1,4,4-tetrakis(3-fluoro-4hydroxyphenyl)butane, 1,1,4,4-tetrakis(3-chloro-4-hydroxyphenyl)butane, 1,1,4,4tetrakis(3-methyl-4-hydroxyphenyl)butane, 1,1,4,4-tetrakis(3-methoxy-4-hydroxyphenyl)butane, 1,1,4,4-tetrakis(3,5-dimethyl-4-hydroxyphenyl)butane, 1,1,5,5-tetrakis(4-hydroxyphenyl)pentane, 1,1,5,5-tetrakis(3-fluoro-4-hydroxyphenyl)pentane, 1,1,5,5-tetrakis(3-chloro-4-hydroxyphenyl)pentane, 1,1,5,5-tetrakis(3-methyl-4-hydroxyphenyl)pentane, 1,1,5,5-tetrakis(3-methoxy-4-hydroxyphenyl)pentane and 1,1,5,5-tetrakis(3,5-dimethyl-4-hydroxyphenyl)pentane. TEP is particularly preferred for practical use.

There are no particular restrictions on solid or liquid guest compounds used in the present invention, if they are compounds that can be taken into holes in the inside of three-dimensional structures formed when atoms or molecules are bound at certain definite composition ratios so as to construct specific structures. Their actual examples include water; alcohols such as methanol, ethanol, isopropanol, n-butanol, n-octanol, 2-ethylhexanol, allyl alcohol, propargyl alcohol, 1,2-butanediol, 1,3-butanediol, 1,4-butanediol, cyclohexanediol, 2-bromo-2-nitropropan-1,3-diol, 2,2-dibromo-2-nitroethanol and 4-chlorophenyl-3-iodopropargyl formal; aldehydes such as formaldehyde, acetaldehyde, n-butylaldehyde, propionaldehyde, benzaldehyde, phthalaldehyde, α-bromocinnamaldehyde and phenylacetaldehyde; and ketones such as acetone, methyl ethyl ketone, diethyl ketone, dibutyl ketone, methyl isobutyl ketone, cyclohexanone, acetylacetone and 2-bromo-4'-hydroxyacetophenone.

Actual examples of the guest compounds also include nitrites such as acetonitrile, acrylonitrile, n-butylonitrile, malononitrile, phenylacetonitrile, benzonitrile, cyanopyridine, 2,2-dibromomethylglutalnitrile, 2,3,5,6-tetrachloroisophthalonitrile, 5-chloro-2,4,6-trifluoroisophthalonitrile and 1,2-dibromo-2,4-dicyanobutane; ethers such as diethyl ether, dibutyl ether, tetrahydrofuran, dioxane, tetrahydropyrane, dioxorane and trioxane; esters such as methyl acetate, ethyl acetate, butyl acetate, n-heptyl acetate and bis-1,4-bromoacetoxy-2-butene; sulfonamides such as benzene sulfonamide; amides such as N-methylformamide, N,N-dimethylformamide, dicyandiamide, dibromonitrilopropionamide, 2,2-dibromo-3-nitrilopropionamide and N,N-diethyl-m-toluamide; halogenated hydrocarbons such as dichloromethane, chloroform, dichloroethylene and tetrachloroethylene; lactams such as ε-caprolactam;lactones such as ε-caprolactone; oxiranes such as arylglycidyl ether; morpholines; and phenols such as phenol, cresol, resorcinol and p-chloro-m-cresol.

Actual examples of the guest compounds also include carboxylic acids and thiocarboxylic acids such as formic acid, acetic acid, propionic acid, oxalic acid, citric acid, adipic acid, tartaric acid, benzoic acid, phthalic acid and salicylic acid; sulfamic acids; thiocarbamic acids; thiosemicarbazides; ureas and thioureas such as urea, phenylurea, diphenylurea, thiourea, phenylthiourea, diphenylthiourea and N,N-dimethyldichlorophenylurea; isothioureas; sulfonylureas; thiols such as thiophenol, allylmercaptan, n-butylmercaptan and benzylmercaptan; sulfides such as benzyl sulfide and butylmethyl sulfide; disulfides such as dibutyl disulfide, dibenzyl disulfide and tetramethylthiuram disulfide; sulfoxides such as dimethyl sulfoxide, dibutyl sulfoxide and dibenzyl sulfoxide; sulfones such as dimethyl sulfone, phenyl sulfone, phenyl-(2-cyano-2-chlorovinyl)sulfone, hexabromodimethyl sufone and diiodomethyl-para-tolyl sulfone; and thiocyanic acids and isothiocyanic acids such as methyl thiocyanate and methyl isothiocyanate.

Actual examples of the guest compounds also include amino acids such as glycine, alanine, leucine, lysine, methionine and glutamine; amide and urethane compounds; acid anhydrides; aromatic hydrocarbons such as benzene, toluene and xylene; alkanes; alkenes; alkynes; isocyanates such as butylisocyanate, cyclohexylisocyanate and phenylisocyanate; thiocyanates and isothiocyanates such as methylenebisthiocyanate and methylenebisisothiocyanate; nitro compounds such as tris(hydroxymethyl)nitromethane; and acyclic aliphatic amines such as ammonia, methylamine, ethylamine, propylamine, butylamine, pentylamine, hexylamine, allylamine, hydroxylamine, ethanolamine, benzylamine, ethylenediamine, 1,2-propanediamine, 1,3-propanediamine, 1,4-butanediamine, 1,5-pentanediamine, 1,6-hexanediamine, diethylenetriamine, triethylenetetramine, tetraethylenepentamine, dipropylenediamine, N,N-dimethylethylenediamine, N,N'-dimethylethylenediamine, N,N-dimethyl-1,3-propanediamine, N-ethyl-1,3-propanediamine, trimethylhexamethylenediamine, alkyl-t-monoamine, menthanediamine, isophoronediamine, guanidine and N-(2-hydroxypropyl)aminomethanol.

Actual examples of the guest compounds also include cyclic aliphatic amines such as cyclohexylamine, cyclohexanediamine, bis(4-aminocyclohexyl)methane, pyrrolidines, azetidines, piperidines, piperazines such as piperazine, N-aminoethylpiperazine and N,N'-dimethylpiperazine, and pyrrolines; cross-linking amines such as 1,8-diazabicyclo[5,4,0]undecen-7,1,5-diazabicyclo[4,3,0]non-5-ene; aromatic amines such as aniline, N-methylaniline, N,N-dimethylaniline, o-phenylenediamine, m-phenylenediamine, p-phenylenediamine, diaminodiphenylmethane, diaminodiphenyl sulfone and m-xylenediamine; modified polyamines such as epoxy compound-added polyamine, Michael-added polyamine, Mannich-added polyamine, thiourea-added polyamine and ketone-blocked polyamine; and imidazoles such as imidazole, 2-methylimidazole, 2-ethylimidazole, 2-isopropylimidazole, 2-n-propylimidazole, 2-ethyl-4-methylimidazole, 1-benzyl-2methylimidazole, 2-undecyl-1H-imidazole, 2-heptadecyl-1H-imidazole, 2-phenyl-1H-imidazole, 4-methyl-2-phenyl-1H-imidazole and 1-benzyl-2-methylimiazole.

Actual examples of the guest compounds also include heterocyclic compounds containing nitrogen such as pyrrole, pyridine, picoline, pyrazine, pyridazine, pyrimidine, pyrazole, triazole, benzotriazole, triazine, tetrazole, purine, indole, quinoline, isoquinoline, carbazole, imidazoline, pyrroline, oxazole, piperine, pyrimidine, pyridazine, benzimidazole, indazole, quinazoline, quinoxaline, phthalimide, adenine, cytocine, guanine, uracil, 2-methoxycarbonylbenzimidazole, 2,3,5,6-tetrachloro-4-methanesulfonylpyridine, 2,2-dithio-bis-(pyridin-1-oxide), N-methylpyrrolidone, methyl 2-benzimidazole carbamate, 2-pyridinethiol-1-oxide sodium, hexahydro-1,3,5-tris(2-hydroxyethyl)-s-triazine, hexahydro-1,3,5-triethyl-s-triazine, 2-methylthio-4-t-butylamino-6-cyclopropylamino-s-triazine, N(fluorodichloromethylthio)phthalimide, 1-bromo-3-chloro-5,5-dimethylhydantoin and 2,4,6-trichlorophenylmaleimide; heterocyclic compounds containing oxygen such as furan, furfuryl alcohol, tetrahydrofurfuryl alcohol, furfurylamine, pyran, coumarin, benzofuran, xanthene and benzodioxane; and heterocyclic compounds containing nitrogen and oxygen such as oxazole, isoxazole, benzoxazole, benzisoxazole, 5-methyloxazoline, 4-(2-nitrobutyl)morpholine and 4,4'-(2-ethyl-2-nitrotrimethylene)dimorpholine.

Actual examples of the guest compounds also include heterocyclic compounds containing sulfur such as thiophene, 3,3,4,4-tetrahydrothiophen-1,1-dioxide, 4,5-dichloro-1,2-dithiolan-3-one, 5-chloro-4-phenyl-1,2-dithiolan-3-one and 3,3,4,4-tetrachlorotetrahydrothiophen-1,1-dioxide; heterocyclic compounds containing nitrogen and sulfur such as thiazolei, benzothiazole, 5-chloro-2-methyl-4-isothiazolin-3-one, 2-methyl-4-isothiazolin-3-one, 4,5-dichloro-3-n-octylisothiazolin-3-one, 2-octyl-4-isothiazolin-3-one, 1,2-benzisothiazolin-3-one, 2-thiocyanomethylbenzothiazole, 2-(4-thiazolyl)benzimidazole and 2-thiocyanomethylbenzothiazole; steroids such as cholesterol; alkaloids such as brucine, quinine and theophylline; natural essential oils such as cineol, hinokitiol, menthol, terpineol, borneol, nopol, citral, citronellol, citronellal, geraniol, menthone, eugenol, linalool and dimethyloctanol; synthetic perfumes such as fragrant olive, jasmine and lemon; and vitamins and their related compounds such as ascorbic acid, nicotinic acid and nicotinamide.

As described above, the process of the present invention for the preparation of a molecular compound having improved stability is a method for producing a molecular compound by mixing and/or kneading a solid host compound with a solid or liquid guest compound. Exemplified is a method carrying out one or more of the steps that (a) a host compound is mixed and/or kneaded with a guest compound, and the product is held at a temperature of 50° C. or higher and the release temperature of the guest compound or below for a fixed period of time; (b) a host compound is mixed and/or kneaded with a guest compound to form a molecular compound which is then washed with a solvent capable of dissolving the guest compound; (c) a solid host compound is pulverized beforehand; and (d) a poor solvent that dissolves a solid host compound, solid guest compound and liquid guest compound poorly is added prior to mixing and/or kneading. Here "a molecular compound having improved stability" refers to a molecular compound able to appropriately control the release of the guest compound from the molecular compound thanks to the improved binding conditions between the host and guest compounds. The method is concretely described below, as an example, when a substance having a catalytic activity to cure a resin is used as a guest compound. A curable resin paint, for example, thermosetting paint such as epoxy paint, contains an epoxy oligomer and a curing catalyst. It becomes difficult to use it as paint at the end if the viscosity rises because of the process of curing the resin while in storage. For example, 2-ethyl-4-methylimidazole (2E4MZ), a curing accelerator for epoxy resins, has excellent catalytic performance of curing, but has a drawback that a paint containing it has a short usable time (pot life), as the resin cures more while in storage if the catalyst coexists with an epoxy oligomer. Because of it, 2E4MZ is used at this moment only for paints of two-liquid type that a catalyst is mixed with a resin immediately before application. It has not been used for paints of one-liquid type that a catalyst and a resin are mixed beforehand. The former has a disadvantage of poor workability, compared with the latter. These facts lead to the conclusion that a molecular compound having improved stability which is formed using a substance with a catalytic activity to cure a resin as a guest compound refers to a molecular compound that does not increase the viscosity of the paint while in storage so that the paint has a long pot life, and has performance excellent in curing a resin by heating or another means when used for coating.

Step (a) mentioned above, that is, a host compound is mixed and/or kneaded with a guest compound, followed by holding the product at a temperature of 50° C. or higher and the release temperature of the guest compound or below for a fixed period of time (hereinafter referred to as "holding with heating"), can improve the stability of the formed molecular compound. For example, in the case of using a substance having a catalytic activity to cure a resin as a guest compound, the degree of the catalytic activity can be controlled appropriately, compared with the case of using the guest compound alone or applying a molecular compound with no treatment of the holding with heating. The result is a greatly prolonged pot life of powder paints and the like. There are no restrictions on the lower limit of the temperature range for the treatment of the holding with heating, if 50° C. or above. It is preferably 70° C. or above. If it is below 50° C., no sufficient effect of improving the stability of the molecular compound is expected. The upper limit of the treatment of the holding with heating, i.e., the release temperature of the guest compound, differs depending on the type of molecular compound. For example, it is in the range between 180 and 200° C. for a molecular compound consisting of TEP and 2E4MZ. In this case, the treatment of the holding with heating is carried out in a temperature range between 50 and 170° C., preferably 70 and 150° C.

Step (b) mentioned above, that is, washing the formed molecular compound with a solvent capable of dissolving the guest compound, preferably capable of dissolving the guest compound without dissolving the host compound, can improve the stability of the molecular compound after washed. For example, when a substance having a catalytic activity to cure a resin is used as a guest compound, the degree of the catalytic activity can be controlled appropriately, compared with the case of using a molecular compound with no treatment of washing. The result is a greatly prolonged pot life of powder paints and the like. There are no particular restrictions on solvents for washing if they can dissolve guest compounds. Preferred are those dissolving guest compounds strongly.

The said Step (c), that is, a solid host compound pulverized by such a means as air jet pulverization is used as a solid host compound when the solid host compound is mixed and/or kneaded with a guest compound to produce a molecular compound, improves the stability of the formed molecular compound. For example, in the case of using a substance having a catalytic activity to cure a resin as a guest compound, the degree of the catalytic activity can be controlled appropriately, compared with the case of using a molecular compound formed from a non-pulverized solid host compound. The result is a greatly prolonged pot life of powder paints and the like. Examples of preferred pulverized products of solid host compounds include solid host compounds of 1.6 μm or smaller, favorably 1.1 μm or smaller, in average particle size; and of 4.0 μm or smaller, favorably 3.7 μm or smaller, in particle size; and 80% by weight of which is 2.0 μm or smaller, favorably 1.8 μm or smaller, in particle size.

Step (d) mentioned above, that is, a poor solvent that dissolves a solid host compound, solid guest compound and liquid guest compound only slightly is added when a host compound is mixed and/or kneaded with a guest compound by a kneader or the like, improves the stability of the formed molecular compound. For example, in the case of using a substance having a catalytic activity to cure a resin as a guest compound, the degree of the catalytic activity can be controlled appropriately, compared with the case of using a molecular compound formed without a poor solvent added. The result is a greatly prolonged pot life of powder paints and the like. Examples of methods for mixing and/or kneading compounds with a poor solvent added include that a host compound is mixed and/or kneaded with a guest compound after adding a poor solvent at an amount of 20 to 200% by weight to the total weight of a solid host compound and a solid or liquid guest compound; that a poor solvent is added and the mixture is mixed and/or kneaded while heating until the content of the solvent becomes 1% by weight or below; and that compounds with a poor solvent added are mixed and/or kneaded and the product is dried so that the content of the solvent is 1% by weight or less. It is particularly preferable to mix and/or knead the host and guest compounds in the coexistence of a poor solvent, and to reduce the content of the solvent in the formed molecular compound to 1% by weight or less. In this way, the formed molecular compound is more improved in stability. There are no particular restrictions on an amount of a poor solvent added. An addition of 200 ml or more and 1000 ml or less, preferably 400 ml or more and 600 ml or less, to a mole of a solid host compound improves the stability of the formed molecular compound. In this case, a molecular compound excellent in stability can be produced even if the content of a poor solvent is a little over 1% by weight. Examples of such poor solvents include solvents that dissolve 1 g/100 ml or less of each of a solid host compound, solid guest compound and liquid guest compound at room temperature. An actual favorable example is water.

There are no particular restrictions on how to mix and/or knead a solid host compound with a solid or liquid guest compound in the afore-mentioned methods for producing molecular compounds. Mixing and/or kneading by a kneader is preferred because of the appropriateness for mass production at a factory scale. The methods of the present invention for producing molecular compounds are characterized in that a kneader is used to mix and/or knead a solid host compound with a solid or liquid guest compound. Descriptions of such kneaders and mixing and/or kneading by a kneader or the like follow.

A kneader used in the present invention can be any equipment that can mix and/or knead a host compound with a guest compound sufficiently at a large scale. Applicable ones include kneaders that are generally used in such fields as food and plastics. A preferred kneader is a device having one or two shafts, capable of mixing and/or kneading substances by rotations of puddles set to the shafts, and with a small clearance between the puddles and the body. More preferred is a kneader quipped with jackets able to cool or heat the equipment body, for example, those described in Japanese Patents Laid-open Nos. Hei 3-86223 and Hei 9-173825. Another type of kneader preferably consists mainly of cylindrical bodies called barrels and screws carrying various screw elements, and usually has a structure of which screws go right through the insides of two or more barrels. The said screw elements are of various types, such as trapezoidal screw element, trapezoidal cut screw element, trapezoidal reverse cut, ball screw element and kneading puddle. These elements are arbitrarily combined. Substances fed into the barrels are moved inside the barrels by the screws, and treated by shearing, mixing or other means by screw elements, such as kneading puddles, in the barrels. A kneader that is generally used in food, plastics and other fields and has basic characteristics such as conveyance, mixing, shearing, compressing, pulverizing and heating functions, can be used as it is. It is particularly preferable to use a twin shaft kneader such as an unengaged anti- or co-directed rotary kneader or a completely or partially engaged anti- or co-directed rotary kneader.

As applicable methods for mixing and/or kneading a host compound with a guest compound using a kneader or the like, a host compound or a guest compound is fed in a kneader or the like and its guest or host compound is added little by little or all at once to mix and/or knead; a host compound and a guest compound are fed simultaneously in a kneader or the like to mix and/or knead; and a host compound is uniformly mixed and/or kneaded with a guest compound beforehand and the mixture is fed in a kneader or the like to mix and/or knead. In the case of mixing and/or kneading a host compound with a guest compound all at once, use of a solid or liquid guest compound at an amount required to form a molecular compound with a solid host compound is advantageous to the removal of unreacted guest compound from reaction system of the host and guest compounds. In addition, if a solid host compound or a solid guest compound has a melting point of 100° C. or below, it is preferable to heat it to melt in a device such as water bath, stir and mix the host and guest compounds to be uniform, and feed the mixture in a kneader to mix and/or knead. As for the degree of uniformity, it is satisfactory if the two compounds are uniformly mixed to the naked eye.

A reaction proceeds promptly, and completes in about 10 to 20 minutes after reaction materials are placed in a device and mixing and/or kneading begins. The reaction proceeds at room temperature. However, the formed molecular compound, if it is very crystalline, may put a huge load on the reaction apparatus as well as impede mixing or kneading. Therefore, a reaction is preferably carried out in a temperature range where a host compound, a guest compound and the formed molecular compound are stable, particularly in the range between 25 and 120° C. In case a reaction proceeds very quickly and the release temperature of a guest compound is high, the place where the host compound contacts the guest compound immediately solidifies. Because of this, the whole compounds may not be uniformly mixed occasionally even if a kneader is used to stir. In such a case, the reaction mixture is once taken out to finely pulverize, and then mixed or kneaded by a kneader again so that a molecular compound can be produced more efficiently.

The molecular compound obtained finally is pulverized at the stage of mixing and/or kneading if it has a high melting point and is very crystalline, and can be used as it is after taken out from the kneader upon the completion of the reaction. It can be pulverized if required. It is possible to granule the formed molecular compound to a specific shape, depending on applications, using an extrusion granulator after mixing and/or kneading regardless of the melting point and crystallinity. Furthermore, it is also possible to hold the obtained molecular compound at a temperature below the decomposition point of the compound for maturing so as to arrange a crystal system or the like for use.

Ordinary extrusion granulators widely used in the fields such as drugs, agricultural chemicals, food or plastic molding can be used in the present invention. Any type including screw, roll, blade, self-molding and ram can be used.

Use of a multi-shaft extruder is preferred in the point of industrial production because of comprehensive operations of mixing, kneading and granulation. The key part of an extruder mainly consists of cylindrical bodies called barrels, dies corresponding to exits, and screws carrying various types of screw elements. A favored extruder usually has a structure that screws go right through the insides of two or more barrels. The said screw elements are of various types, such as trapezoidal screw element, trapezoidal cut screw element, trapezoidal reverse cut, ball screw element and kneading puddle. These elements are combined arbitrarily. Substances fed into barrels are moved inside the barrels by the screws; treated by shearing, mixing or other means in the barrels by screw elements, such as kneading puddles; and extruded from fine pores of the dies. Usually the barrels and dies are each independently temperature controlled.

The number of rotations of screw can be arbitrarily set depending on a model and type of an extruder, materials used, shapes of screws and other conditions. An exhaust die can be changed as required, depending on purposes. To put it concretely, circular exhaust dies with various diameters can be used to produce cylindrical products, and flat exhaust dies for sheet-shaped products. Actual examples of models of multi-shaft extruders include Laboruder Mark II (manufactured by Nippon Seikosho Co., Ltd.) and PCM Series twin shaft extruders (manufactured by Ikegai Co., Ltd.).

There are no particular restrictions on processes of the present invention for the preparation of the molecular compounds, if a compound which is pulverized to an average particle size of 1.6 μm or smaller beforehand or pulverized to a particle size of 4.0 μm or less beforehand, or 80% by weight of which is pulverized to 2.0 μm or smaller in particle size in advance is used as a solid host compound, and dispersed together with a solid or liquid guest compound in a poor solvent that dissolves the solid host compound and the solid or liquid guest compound only slightly.

Any reaction solvent can be used in the present invention if it is a poor solvent. Examples of poor solvents are solvents that dissolve 1 g/100 ml or less of a host compound or a guest compound at room temperature. An actual example is water. An amount of a poor solvent used can be arbitrarily decided, depending on a host compound and a guest compound that are involved in a reaction and a molecular compound to be formed. There are no particular restrictions on the amount if a solid host compound and a guest compound are dispersed satisfactory. A preferred amount is that a solid host compound is from 10 to 50% by weight in concentration. When a molecular compound is produced in the coexistence of a poor solvent, it is particularly preferable to reduce the content of the poor solvent in the formed molecular compound to 1% by weight or less for the stability of the formed. If an amount of a poor solvent used is within the aforementioned range, a molecular compound excellent in stability can be obtained even if the content of the poor solvent in the formed molecular compound is a little more than 1% by weight.

Any host compound that is pulverized beforehand can be reacted in the said solvent. Examples are host compounds of 1.6 μm or smaller, preferably 1.1 μm or smaller, in average particle size, and 4.0 μm or less, preferably 3.7μ or less, in particle size. Another example is a host compound 80% by weight of which is 2.0 μm or smaller, preferably 1.8 μm or smaller, in particle size. Use of a solid host compound with such a particle size improves the stability of the formed molecular compound. For example, a stable molecular compound having a composition ratio similar to that of a molecular compound produced using a non-pulverized host compound in a reaction solvent of methanol can be obtained.

It is desirable to pulverize a host compound by a jet stream. An Ulmax pulverizer is exemplified to use for pulverization.

An Ulmax pulverizer pulverizes ultra fine powder of several microns or less without contaminating it by taking individual particles into a supersonic jet stream produced by issuing compressed gas, such as high-pressure gas or high-pressure air, from a special nozzle. Use of such an Ulmax pulverizer makes it possible to pulverize substances with low melting points because temperature lowers due to adiabatic expansion when high-pressure gas is issued from a nozzle so that pulverization produces less heat. A host compound pulverized by such an Ulmax pulverizer produces a molecular compound having improved stability.

A reaction temperature is in a temperature range of room temperature or above, preferably 50° C. or above, to the release temperature of a guest compound or below in a reaction solvent. The upper limit of the reaction temperature, the release temperature of a guest compound, differs depending on a type of molecular compound. For example the release temperature of a molecular compound consisting of TEP and 2-ethyl-4methylimidazole is in a range of 180 to 200° C. A molecular compound formed within the temperature range can be improved in stability. For example, as described later, when a molecular compound containing a substance with a catalytic activity to cure a resin as a guest compound is added to a thermosetting paint or the like, the degree of the catalytic activity is properly controlled, compared with direct use of the guest compound, and a pot life of powder paint or the like is greatly prolonged.

A molecular compound produced according to the said method exists stably on its own. The two constituent compounds composing the molecular compound are bound through hydrogen bonds and dissociate easily to the original compounds by simple operations. It is usually a crystalline solid, and may be amorphous or liquid. It may also be in polymorphism. The production methods of the present invention are applicable regardless of these forms.

The molecular compounds produced according to the production methods of the present invention have improved binding conditions between the host and guest compounds and can be properly controlled for the release of the guest compounds from the molecular compounds.

The molecular compounds produced according to the said production methods are, as mentioned above, favorably applied, for example, as substances to control resin curing rates.

The molecular compounds of the present invention can be used in any form. For example, two or more molecular compounds each composing different constituent compounds, are mixed to use. The molecular compounds of the present invention may be used together with other substances, as long as target functions are not damaged. Another way to use the molecular compounds of the present invention is adding excipients or the like to the compounds for molding granules or tablets. Further, the compounds may also be used to add to plastics, paints, and their raw materials and material compositions. In addition, the molecular compounds of the present invention may also be used, as they are, as starting materials for organic syntheses, or as specific reaction sites.

A clathrate compound consisting of, for example, 3,3'-bis(phenylsulfonyl)-4,4'dihydroxyphenyl sulfone as a host compound and, as a guest compound, an isothiazolone germicide such as 5-chloro-2-methyl-4-isothiazolin-3-one or 2-methyl-4-isothiazolin-3-one; antimicrobial agent, insecticide or moth proofing agent such as hinokitiolor 1,8-cineol; perfume such as rosemary; anti-fouling agent such as an isothiazolone compound; catalyst including a curing agent for resins such as phthalic anhydride or tetrahydrophthalic anhydride; or curing accelerator for epoxy resins such as 1,8-diazabicyclo[5,4,0]undecene-7,1,5-diazabicyclo[4,3,0]non-5-ene or 2-ethyl-4imidazole; or an organic solvent such as toluene, xylene or pyridine, is newly endowed with functions such as prolongation of release, reduction of skin irritation, chemical stabilization, nonvolatilization, powderization and selective separation of useful substances, in addition to the actions that the guest compound has originally. Therefore, the clathrate compound is very useful as a germicide, antibacterial agent, insecticide, moth proofing agent, perfume, anti-fouling agent, catalyst such as curing agent for epoxy resins and organic solvent, with new characteristics.

BRIEF DESCRIPTIONS OF FIGURES

BEST FORMS TO IMPLEMENT THE INVENTION

The present invention is described in detail in reference to Examples, but not limited to the Examples.

EXAMPLE 1

Preparation of a Molecular Compound Using a Kneader

Figure 1:
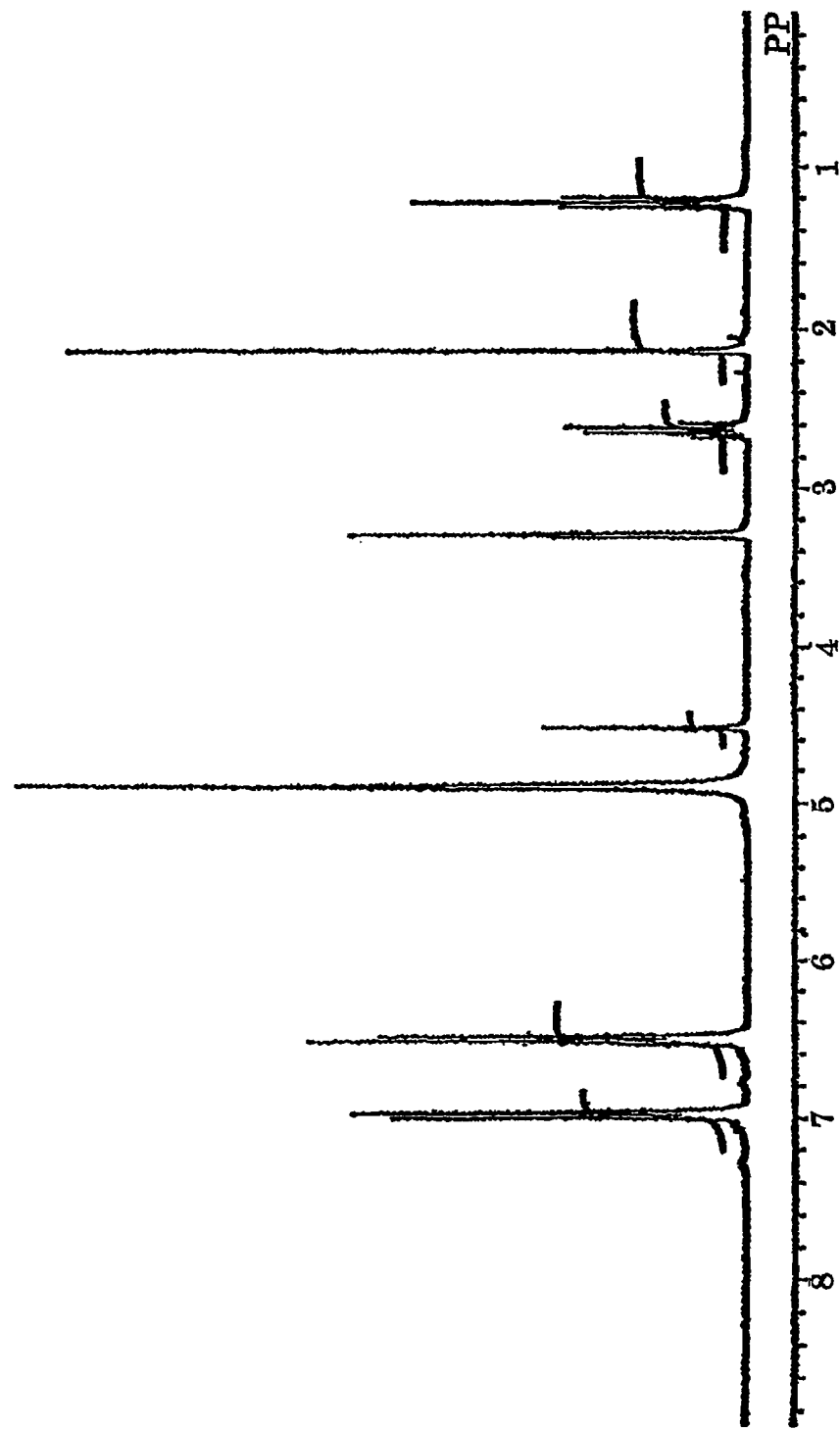
FIG. 1 shows a $^1$H-NMR spectrum of the molecular compound composing TEP and 2-ethyl-4-methylimidazole of a composition ratio of 1:2 (mole ratio), of Example 1 of the present invention (where DMSO-$d_6$ is used as a solvent).
Figure 2:
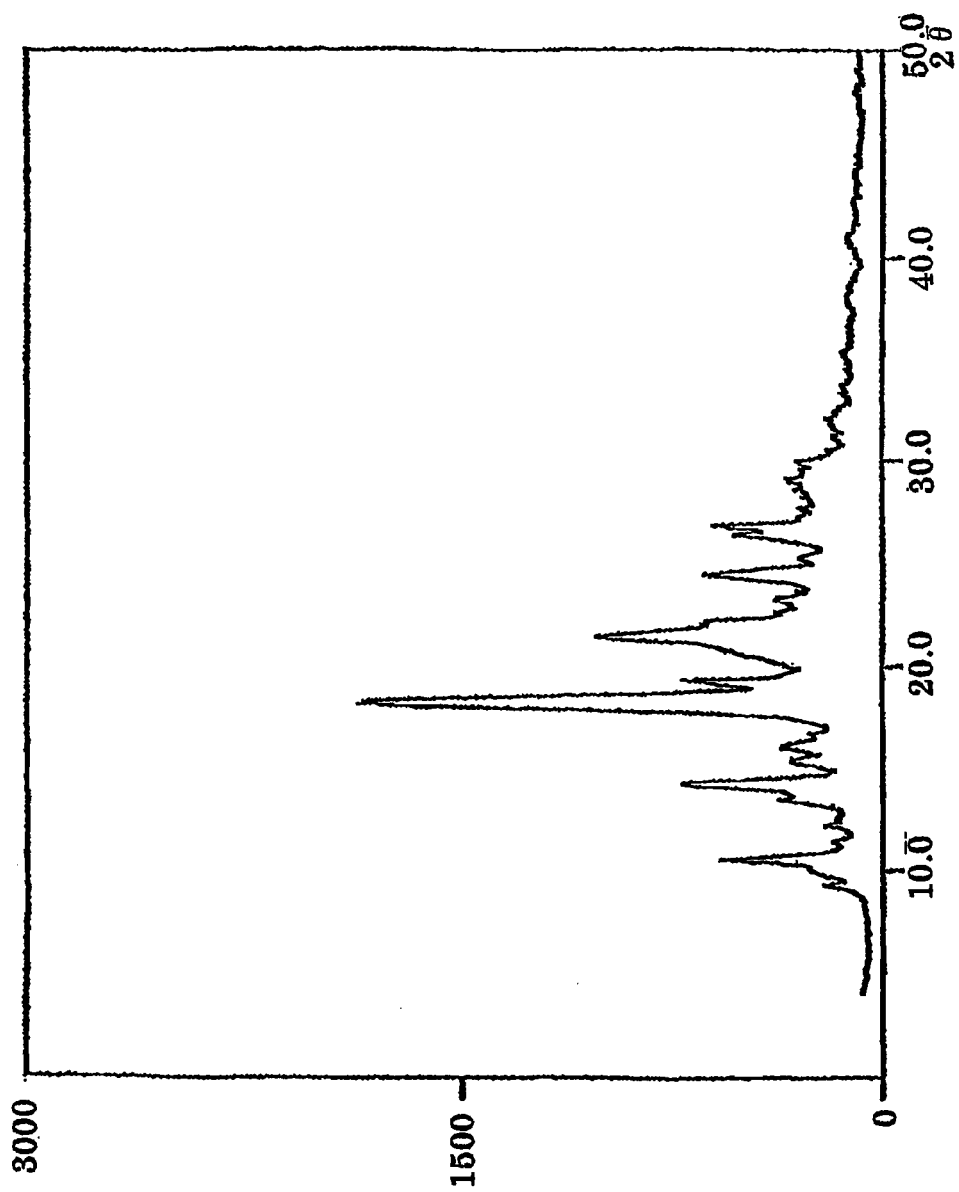
FIG. 2 shows a powder X-ray diffraction pattern of the molecular compound composing TEP and 2-ethyl-4-methylimidazole of a composition ratio of 1:2 (mole ratio), of Example 1 of the present invention.

A curing accelerator for epoxy resins, 2-ethyl-4-methylimidazole (2E4MZ), was used as a guest compound. 17.0 g (150 mmol, purity: 97%) of 2E4MZ was heated to melt, and added to 33.3 g (75 mmol, purity: 90%) of TEP while stirring well, followed by stirring for another 5 minutes. The obtained mixture was fed little by little to the mixer of a kneader (Brabender Plasti-corder Model PLV 151, manufactured by Brabender Co., Ltd.) set to 25° C., while rotating the rotor. The mixture was further stirred for 10 minutes after all the mixture was added. The reaction product was taken out. The measurements of the product by $^1$H-NMR and powder X-ray diffraction showed the formation of a molecular compound consisting of the host and guest compounds at a ratio of 1:2. Measurements of the TG-DTA of the reaction product for the thermal behavior confirmed that a molecular compound was formed as a weight loss was seen at 180° C. A $^1$H-NMR spectrum is shown in FIG. 1 and a powder X-ray diffraction pattern in FIG. 2, respectively.

EXAMPLE 2

Preparation of a Molecular Compound Using a Kneader (Examination of Kneading Temperature)

Example 1 was repeated except that the kneading temperature was changed to 70° C., 100° C. or 120° C. The obtained molecular compound had the same results of the TG-DTA and powder X-ray diffraction measurements as those of the molecular compound in Example 1. This showed no difference in reactivity of TEP with 2E4MZ in the reaction, depending on reaction temperature.

EXAMPLE 3

Preparation of a Molecular Compound Using a Kneader (Examination of Ratios of Blending Amounts of Host and Guest Compounds)

Example 1 was repeated except that 8.5 g (75 mmol, purity: 97%) of 2E4MZ was used. The obtained molecular compound was a mixture of the host and guest compounds at a ratio of 1:2. This showed that the obtained molecular compound was always at a fixed composition ratio, even if a mixing ratio of a guest compound with a host compound was changed. 8.5 g (75 mmol, purity: 97%) of melted 2E4MZ was added to the said mixture of the host and guest compounds at the ratio of 1:2, and mixed. The product was subject to the same instrumental analyses as those in Example 1. The obtained molecular compound consisted of the host and guest compounds at a ratio of 1:2.

EXAMPLE 4

Preparation of a Molecular Compound Using a Kneader 222.0 g (510 mmol, purity: 91.5%) of TEP was placed in a bench kneader (manufactured by Irie Syoukai Co., Ltd.). 114.6 g (1.02 mol, purity: 98.05%) of 2E4MZ was heated to melt and fed to the kneader with stirring, followed by further stirring for 20 minutes. A sample was taken from each of three arbitrary places. Then the mixture was heated to 90° C., stirred for 20 minutes to complete the reaction, and cooled. The products were subjected to the same instrumental analyses as those in Example 1. Measurements of the samples taken before heating showed no formation of molecular compounds. The product obtained after the completion of the reaction was proved to be a molecular compound consisting of the host and guest compounds at a ratio of 1:2 by the measurements of $^1$H-NMR and powder X-ray diffraction.

EXAMPLE 5

Preparation of a Molecular Compound Using a Kneader

Figure 3:
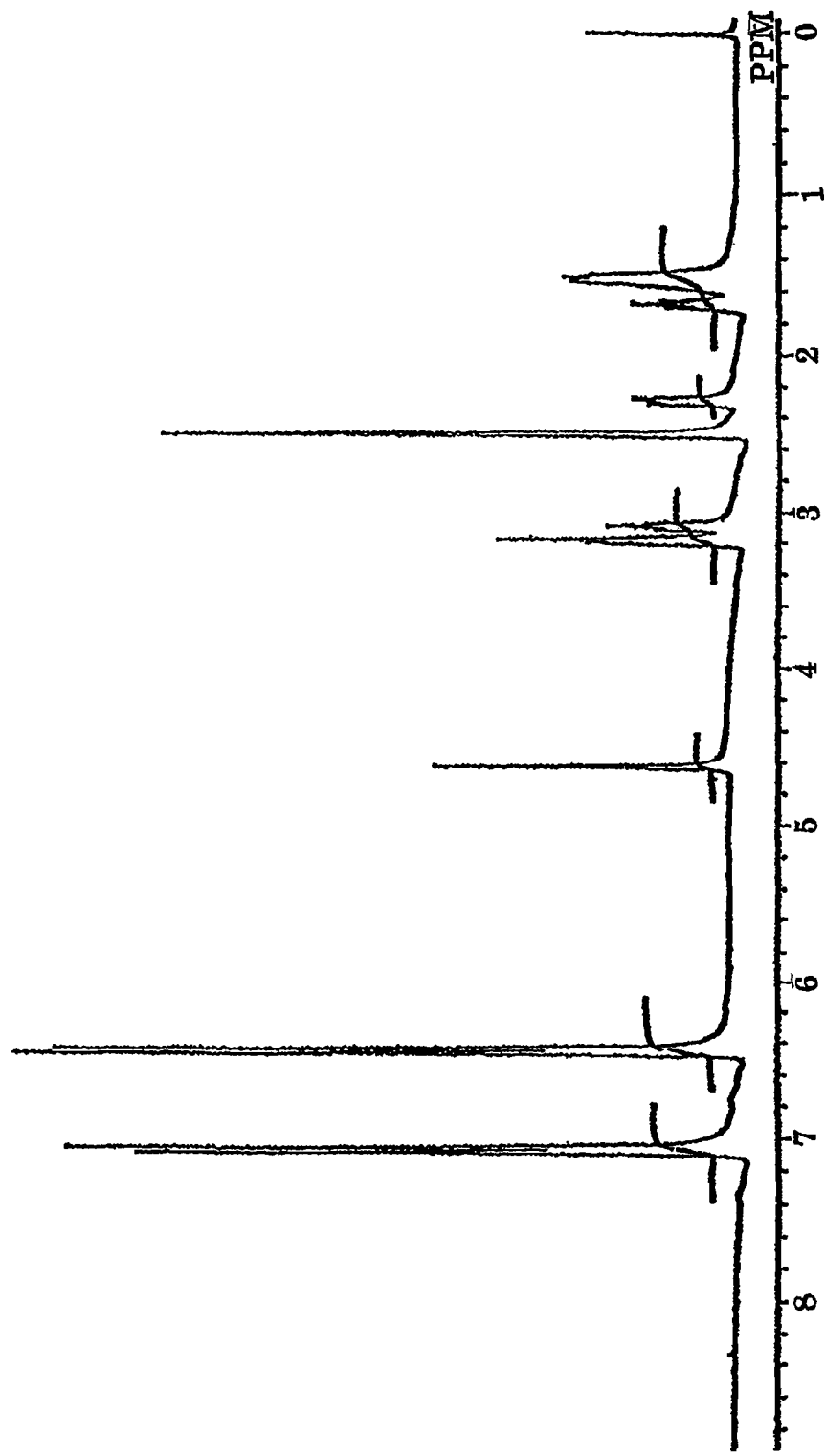
FIG. 3 shows a $^1$H-NMR spectrum of the molecular compound composing TEP and 1,8-diazabicyclo[5,4,0]-undecene-7 (DBU) of a composition ratio of 1:2 (mole ratio), of Example 5 of the present invention (where DMSO-$d_6$ is used as a solvent).
Figure 4:
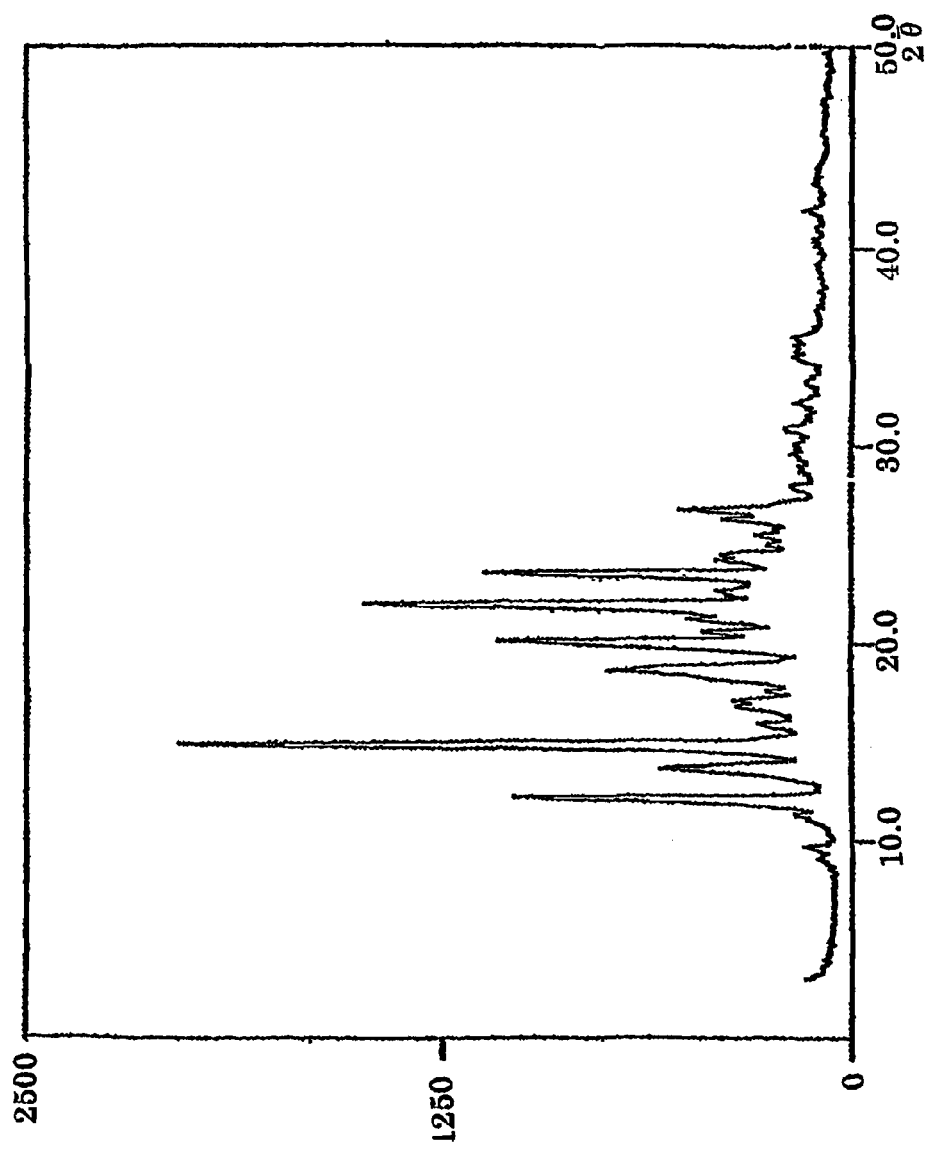
FIG. 4 shows a powder X-ray diffraction pattern of the molecular compound composing TEP and 1,8-diazabicyclo[5,4,0]-undecene-7 (DBU) of a composition ratio of 1:2 (mole ratio), of Example 5 of the present invention.

A curing accelerator for epoxy resins, 1,8-diazabicyclo[5,4,0]-undecene-7 (DBU), was used as a guest compound. 22.9 g (150 mmol, purity: 99%) of DBU was added to 33.3 g (75 mmol, purity: 90%) of TEP, while stirring well, and stirred for another 5 minutes. The obtained mixture was fed little by little to the mixer of a kneader (Brabender Plasti-corder Model PLV 151, manufactured by Brabender Co., Ltd.) set to 100° C., while rotating the rotor. It was further stirred for 10 minutes after all the mixture was added. The reaction product was taken out. The measurements of the product by $^1$H-NMR and powder X-ray diffraction showed the formation of a molecular compound consisting of the host and guest compounds at a ratio of 1:2. The measurements of the TG-DTA of the reaction product for the thermal behavior confirmed that a molecular compound was formed as a weight loss was seen at 169° C. and 316° C. A $^1$H-NMR spectrum is shown in FIG. 3 and a powder X-ray diffraction pattern in FIG. 4, respectively. The mixture before being kneaded by the kneader was subjected to TG-DTA measurements for the thermal behavior. The results suggested that a molecular compound was partially formed as a weight loss was observed at three steps from 124° C.

EXAMPLE 6

Preparation of a Molecular Compound According to Step (a)

A 1-L bench kneader (manufactured by Irie Syoukai Co., Ltd.) was heated to 82° C. 106.7 g (0.95 moles) of melted 2E4MZ (purity: 98.05%) was fed in the kneader with stirring, and 203.5 g (0.5 mol) of TEP (purity: 97.9%) was added to it. The mixture was mixed with stirring for 2 hours at the same temperature to give a molecular compound. The compound taken out from the kneader weighed 289.7 g. The results of $^1$H-NMR measurements of the obtained molecular compound showed a molar ratio of TEP to 2E4MZ to be 1:1.85. The molecular compound was held in an oven heated to 70° C. A sample was taken in a week, 3 weeks, 4 weeks and 6 weeks for the evaluation of the catalytic activity of 2E4MZ as a curing accelerator for epoxy resins. For comparison, a sample taken immediately after the molecular compound was formed, as well as a sample of 2E4MZ itself as control, were subjected to catalytic activity evaluations. The said evaluations of catalytic activities were carried out according to [Test of catalytic activities by measuring the pot life of epoxy resin] and [Test of catalytic activities by examining epoxy resin curing conditions] described below. The results of these tests are shown in Tables 1 and 2.

[Test of Catalytic Activities by Measuring the Pot Life of Epoxy Resin]

A powder paint of thermosetting resin, such as epoxy powder paint, contains an epoxy oligomer and a curing catalyst, such as 2E4MZ. It becomes difficult to use the powder paint at the end as paint if the resin has been curing while in storage. A desirable curing catalyst used has performance of promptly curing the resin by means of heating or the like when applied, without increasing the viscosity while in storage. (2E4MZ has excellent performance as a curing catalyst, but a drawback that a paint containing it has a short pot life. Because of this, it has never actually been used to date.) A pot life, one of indicators to evaluate curing catalysts, was measured for the evaluation of the performance of the molecular compounds of the present invention: Adeka resin EP4100E (produced by Asahi Denka Kogyo Co., Ltd.) was used as an epoxy oligomer. 100 g of epoxy resin before cured was placed in a mayonnaise glass jar and immersed for an hour in a thermostatic water bath set to 35° C. beforehand. To the jar was added a molecular compound containing 3% by weight of 2E4MZ to mix well for 5 minutes. Viscosity was measured with time while the jar was kept immersed in the water bath. A time when the initial viscosity was doubled was regarded as the pot life. The thermostatic water bath used was a circulation type thermostatic water bath TRL-40SP made by Thomas Kagaku Kikai Co., Ltd and the viscometer was a B-type viscometer made by Tokyo Keiki Co., Ltd.

[Test of Catalytic Activities by Examining Epoxy Resin Curing Conditions]

To directly study the performance of curing catalyst, a test of catalytic activities was carried out by measuring differential scanning calories (DSCs). Adeka resin EP 4100E (produced by Asahi Denka Kogyo Co., Ltd.) was used as an epoxy oligomer. 20 g of non-cured epoxy resin was placed in a mayonnaise glass jar. A molecular 23 compound containing 3% by weight of 2E4MZ was added to it and mixed well for 5 minutes. The mixture was subjected to DSC measurements. A differential scanning calorimeter (Model DSC 220C made by Seiko Instruments Co., Ltd.) was used under the conditions that an amount of sample used was 3 to 4 mg, measuring temperatures were in the range of 30 to 300° C., temperature rising rate was at 20° C./min, measuring atmosphere was in a flow of $N_2$ (30 ml/min), and a sealed aluminum pan was used.

TABLE 1

| Sample/ 70° C. holding time | Molecular compound | | | | | 2E4MZ Alone |
|---|---|---|---|---|---|---|
| | Immediately after produced | 1 week | 3 weeks | 4 weeks | 6 weeks | |
| Pot life (hrs) | 11 | 76 | 168 | 106 | 140 | 7 |

TABLE 2

| | Sample (molecular compound) | |
|---|---|---|
| | Held at 70° C. for 6 weeks | Immediately after produced |
| Curing temperature (° C.) | 124-203 | 117-203 |
| Top peak temperature (° C.) | 152 | 151 |
| Temperature to top peak (° C.) | 28.6 | 34.4 |
| Calorific value (mj/mg) | 216.7 | 221.8 |

Table 1 shows the results of the measurements of the pot lives of the epoxy resin. As seen from the table, the pot life was greatly prolonged when samples taken from the product kept heating at 70° C. for 1 to 6 weeks were used, compared to that of the sample taken immediately after the molecular compound was formed, that is, no holding period, and a sample from 2E4MZ itself. It is therefore understood that holding a molecular compound with heating after formed improves the stability of the compound. The effect of improving the stability is considered to be due to stronger clathrate conditions thanks to the treatment of holding with heating. Table 2 shows the results of the tests for curing the epoxy resin. It is understood from the table that the treatment of holding with heating had hardly any effect on curing the epoxy resin, and that the polymerization starts early and the curing rate became quicker as the temperature range to the top peak (° C.) is rather narrower.

EXAMPLE 7

Preparation of a Molecular Compound According to Step (b)

A 1-L bench kneader (manufactured by Irie Syoukai Co., Ltd.) was heated to 80° C. 106.7 g (0.95 moles) of melted 2E4MZ (purity: 98.05%) was fed in the kneader with stirring, and 60.0 g of TEP (purity: 97.9%) was added to it. The mixture was mixed with stirring for an hour at the same temperature. 60.0 g of TEP was further added and mixed with stirring for 2 hours at the same temperature. Furthermore, 83.5 g (total: 203.5 g, 0.5 moles) of TEP was added to continuously mix with stirring for 12 hours to give a molecular compound. 20 g of the obtained molecular compound was added to each of 20 ml of xylene and 50 ml of n-hexane. Both of the solvents dissolve 2E4MZ. The mixtures were separately stirred for 20 minutes. The solid was each separated by filtration, and dried at 100° C. under reduced pressure for 30 minutes to give 19.0 g of the product washed with xylene and 18.8 g of the product washed with n-hexane. Samples taken from the washed products and from the products before washed were subjected to catalytic activity evaluations by the same methods as those used in Example 6. The results are shown in Tables 3 and 4. The $^1$H-NMR measurements of the molecular compounds after washed with xylene and with n-hexane showed molar ratios of TEP to 2E4MZ to be 1:1.85 and 1:1.58, respectively.

TABLE 3

| | Sample | | |
|---|---|---|---|
| | Washed with xylene | Washed with n-hexane | Not washed |
| Pot life (hours) | 112 | 106 | 34 |

TABLE 4

| | Sample (molecular compound) | | |
|---|---|---|---|
| | Washed with xylene | Washed with n-hexane | Not Washed |
| Curing temperature (° C.) | 120-204 | 117-202 | 115-204 |
| Top peak temperature (° C.) | 151 | 152 | 151 |
| Temperature to top peak (° C.) | 30.9 | 35 | 36.1 |
| Calorific value (mj/mg) | 333.4 | 347.5 | 332.5 |

Table 3 shows the results of the measurements of the pot lives of the epoxy resin, and reveals that use of the sample of the molecular compound washed with xylene or n-hexane resulted in much more prolonged pot life of the paint, compared with the sample taken from the non-washed product after the molecular compound was formed. This indicates that washing of the molecular compound with xylene or n-hexane after it was produced improved the stability of the molecular compound. The effect on the stability improvement is considered to be due to removal of unreacted 2E4MZ by washing with xylene or n-hexane. The results of the test for curing the epoxy resin are shown in Table 4. The washings hardly affect on the curing of the epoxy resin. It is therefore understood that washed products can be used advantageously as curing catalysts for powder paints, when a pot life is taken into account.

EXAMPLE 8

Preparation of a Molecular Compound According to Step (c)

A 1-L bench kneader (manufactured by rrie Syoukai Co., Ltd.) was heated to 82.3° C. 150 g (0.37 moles) of TEP (purity: 97.9%), pulverized with a jet stream by an Ulmax pulverizer ("Ulmax air jet pulverizer" manufactured by Nisso Engineering Co., Ltd.) was fed in the kneader. The particle size distributions of TEP before and after the air jet pulverization are shown in Table 5. 78.65 g (0.70 moles) of melted 2E4MZ (purity: 98.05%) was fed with stirring, and kept on stirring at the same temperature. A sample was taken at 1.0, 2.5 and 4.5 hours, and subjected to catalytic activity evaluations by the same methods as those used in Example 6. The results are shown in Tables 6 and 7.

TABLE 5

| Particle size (μm) | Cumulative weight % | |
| --- | --- | --- |
| | After pulverization | Before pulverization |
| 0.90 or smaller | 36.36 | 19.94 |
| 1.10 or smaller | 50.28 | 28.43 |
| 1.30 or smaller | 61.53 | 35.98 |
| 1.50 or smaller | 70.55 | 42.70 |
| 1.80 or smaller | 80.86 | 51.50 |
| 2.20 or smaller | 90.06 | 61.24 |
| 2.60 or smaller | 85.46 | 69.18 |
| 3.10 or smaller | 98.79 | 76.78 |
| 3.70 or smaller | 100.00 | 83.68 |
| 4.30 or smaller | 100.00 | 88.70 |
| 5.00 or smaller | 100.00 | 92.91 |
| 6.00 or smaller | 100.00 | 96.90 |
| 7.50 or smaller | 100.00 | 99.75 |
| 9.00 or smaller | 100.00 | 100.00 |

TABLE 6

| | Sample/(kneading time) | | | |
| --- | --- | --- | --- | --- |
| | Not pulverized | Pulverized by jet stream | | |
| | 2 hours | 1 hour | 2.5 hours | 4.5 hours |
| Pot life (hours) | 11 | 48 | 60 | 70 |

TABLE 7

| | Sample (molecular compound) | | |
| --- | --- | --- | --- |
| | Pulverized by jet stream | | Not pulverized |
| Kneading time (hours) | 1.0 | 4.5 | 2.0 |
| Curing temperature (° C.) | 117-203 | 117-198 | 117-203 |
| Top peak temperature (° C.) | 151 | 151 | 151 |
| Temperature to top peak (° C.) | 33.8 | 33.8 | 34.4 |
| Calorific value (mj/mg) | 190 | 191 | 221.8 |

Table 6 shows the results of the measurements of the pot lives of the epoxy resin. As apparent from the table, the pot life was prolonged when the sample taken from the molecular compound prepared using the host compound pulverized by a jet stream was used, compared with the sample of the molecular compound formed with the non-pulverized host compound. It is understood that the molecular compound is improved in stability when the compound pulverized by a jet stream is used as the host compound, and particularly when the compound pulverized by a jet stream is used as the host compound and kneaded with the guest compound for a longer period of time. It is considered that use of the host compound treated by air jet pulverization results in a homogeneous molecular compound so as to improve the stability. Table 7 shows the results of the test for curing the epoxy compound. From the table, use of the host compound pulverized by a jet stream hardly affected the curing of the epoxy resin. It is therefore understood that the molecular compound produced using the host compound pulverized by a jet stream can be advantageously used as a curing catalyst for powder paints when the improvement of the pot life is taken into account.

EXAMPLE 9

Preparation of a Molecular Compound According to Step (d)

A 1-L bench kneader (manufactured by Irie Syoukai Co., Ltd.) was heated to 80° C. 203.5 g (0.50 moles) of TEP (purity: 97.9%) was fed in the kneader. 250 ml of water was added to it to mix with stirring for 10 minutes. 106.7 g (0.95 moles) of melted 2E4MZ (purity: 98.05%) was added all at once. The mixture was stirred at 80° C. for 4 hours. The powder taken out weighed 294 g. The obtained powder was dried under vacuum at 70° C. for 5 hours. The powder after dried weighed 293 g and the moisture content was 0.25% by weight. The results of $^1$H-NMR measurements of the obtained molecular compound showed a molar ratio of TEP to 2E4MZ to be 1:1.68. The dried product was subjected to catalytic activity evaluations by the same methods as those used in Example 6. The results, together with those of Example 10, are shown in Tables 8 and 9.

EXAMPLE 10

Preparation of a Molecular Compound According to Step (d)

A 1-L bench kneader (manufactured by Irie Syoukai Co., Ltd.) was heated to 80° C. 203.5 g (0.50 moles) of TEP (purity: 97.9%) was fed in the kneader. 250 ml of water was added to it to mix with stirring for 10 minutes. 112.32 g (1.0 mole) of 2E4MZ (purity: 98.05%) was added over 5 minutes. The mixture was mixed with stirring at 80° C., and a sample was taken at 2.5 hours and 5 hours. The moisture contents of the samples, measured by an ordinary method, were 0.23% by weight and 0.21% by weight, respectively. The samples were subjected to catalytic activity evaluations by the same methods as those used in Example 6. The results, together with those of Example 9, are shown in Tables 8 and 9.

TABLE 8

| | Sample/(kneading time) | | |
| --- | --- | --- | --- |
| | Example 9 | Example 10 | |
| | 4 hours | 2.5 hours | 5 hours |
| Moisture content (% by weight) | 0.25 | 0.23 | 0.21 |
| Pot life (hours) | 100 | 59 | 71 |

TABLE 9

| | Sample (molecular compound) | |
| --- | --- | --- |
| | Example 9 | Example 10 |
| Kneading time (hours) | 4.0 | 5 |
| Curing temperature (° C.) | 128-207 | 124-204 |
| Top peak temperature (° C.) | 154 | 153 |
| Temperature to top peak (° C.) | 26.9 | 29.2 |
| Calorific value (mj/mg) | 411.5 | 273.9 |

Table 8 shows the results of the measurements of the pot lives of the epoxy resin. It is apparent from the table, in the case of using the sample (Example 9) taken from the product obtained by adding water to the host and guest compounds to mix before drying, or the sample (Example 10) taken from the molecular compound that was formed in a way that the starting materials with water added were mixed while heating to reduce the moisture content to 1% by weight or less, the pot lives were lengthened, compared with that when the sample of the product produced without water added was used. It is therefore understood that stirring, mixing and kneading of the host compound with the guest compound in the presence of water improve the stability of the molecular compound. A reason for the stability improvement is considered to be because of the homogenized molecular compound thanks to the reaction carried out in the presence of water. The results of the test for curing the epoxy resin, shown in Table 9, reveal almost no effect of stirring, mixing and kneading in the presence of water on curing the epoxy resin. It is thus understood that the molecular compound prepared by stirring, mixing and kneading the starting materials in the presence of water can be advantageously used as a catalyst for curing powder paints.

EXAMPLE 11 TO 14

Preparation of a Molecular Compound According to Step (d)

A 1-L bench kneader (manufactured by Irie Syoukai Co., Ltd.) was heated to a temperature specified in Table 10. 203.5 g (0.50 moles) of TEP (purity: 97.9%) was fed in the kneader. 250 ml of water was added to it to mix with stirring for 3 minutes. Continuing stirring, 106.7 g (0.95 moles) of melted 2E4MZ (purity: 98.05%) was added all at once. The mixture was continuously mixed with stirring at the specified temperature. A sample was taken at a fixed reaction time shown in Table 10. The samples were subjected to catalytic activity evaluations by the same methods as those 29 used in Example 6. Part of the sample taken at the fixed time was dried at 75° C. for 4 hours and subjected to the catalytic activity evaluation. The results are shown in Tables 10 and 11.

TABLE 10

| | | Example 11 | | Example 12 | | Example 13 | | Example 14 | |
|---|---|---|---|---|---|---|---|---|---|
| | | Reaction temp (° C.) | | | | | | | |
| | | 84-86 | | 52.8-64 | | 35-46.8 | | 25-27 | |
| | Reaction time (hours) | $H_2O$ (wt %) | Pot life (hours) | $H_2O$ (wt %) | Pot life (hours) | $H_2O$ (wt %) | Pot life (hours) | $H_2O$ (wt %) | Pot life (hours) |
| Before dried | 1.0 | 16.4 | 15 | 34.3 | | 37.8 | | | |
| | 2.5 | 0.34 | 150 | 22.3 | 10 | 31.2 | | 36.3 | |
| | 4.5 | 0.25 | 160 | 031 | 128 | 17.1 | 9 | 31.9 | |
| | 6.5 | | | | | 0.35 | 125 | 26.2 | 21 |
| After dried | 1.0 | 0.20 | 134 | 0.22 | 128 | 0.21 | 82 | | |
| | 2.5 | | | 0.25 | 147 | 0.22 | 132 | 0.21 | 68 |
| | 4.5 | | | | | 0.20 | 132 | 0.29 | 105 |
| | 6.5 | | | | | | | 0.21 | 123 |

TABLE 11

| | | Example 11 | | Example 12 | | Example 13 | | | Example 14 | |
|---|---|---|---|---|---|---|---|---|---|---|
| | | Reaction temp (° C.) | | | | | | | | |
| | | 84-86 | | 52.8-64 | | 35-46.8 | | | 25-27 | |
| | | Kneading time (hours) | | | | | | | | |
| | | 1.0 | 4.5 | 2.5 | 4.5 | 1.0 | 4.5 | 6.5 | 2.5 | 6.5 |
| Before dried | Moisture content (wt %) | 16.4 | 0.25 | 22.3 | 0.31 | 37.8 | 17.1 | 0.35 | 36.3 | 26.2 |
| | Curing temperature | 113-204 | 124-206 | | 123-206 | | 109-202 | 123-203 | | |
| | Top peak temp. (° C.) | 153 | 154 | | 153 | | 152 | 153 | | |
| | Temp. to top peak (° C.) | 40.8 | 29.6 | | 30.7 | | 43.1 | 29.6 | | |
| | Calorific value (mj/mg) | 178.5 | 317.8 | | 285.8 | | 138.3 | 224.5 | | |
| After dried | Moisture content (wt %) | 0.20 | | 0.25 | | 0.21 | 0.20 | | 0.21 | 0.21 |
| | Curing temperature | 122-206 | | 126-206 | | 121-206 | 126-201 | | 120-206 | 123-200 |
| | Top peak temp. (° C.) | 154 | | 154 | | 153 | 153 | | 152 | 153 |
| | Temp. to top peak (° C.) | 31.9 | | 27.9 | | 31.4 | 26.7 | | 31.5 | 29.5 |
| | Calorific value (mj/mg) | 298 | | 261.2 | | 309.8 | 240.9 | | 291.8 | 230.8 |

Table 10 shows the results of the measurements of the pot lives of the epoxy resin. It is apparent for the table that the pot lives of the epoxy resin were greatly prolonged when the samples were used from the molecular compounds with the moisture contents of 1% by weight or less that were produced in a way that the host compound was reacted with the guest compound by stirring, mixing and kneading in the presence of water so as to have the moisture content of 1% by weight or less or that the reaction products were dried to have moisture content of 1% or less, regardless of the reaction temperatures, compared with the samples with the moisture contents exceeding 1% by weight. It is therefore understood that the molecular compounds produced in the presence of water and having moisture contents of 1% by weight or less are improved in stability. The stability is considered to be improved because the molecular compounds are homogenized by the reaction of the compounds in the presence of water and reducing the moisture contents to 1% by weight or less. Table 11 shows the results of the test for curing the epoxy resin. It also reveals that the samples taken from the molecular compounds with the moisture contents of 1% by weight or less result in higher curing temperatures, narrower temperature ranges to the top peaks and larger calorific values of the paint than the samples taken from the molecular compounds with the moisture contents exceeding 1% by weight did. Therefore, curing of the epoxy resin started sharply and promptly. It is understood that the molecular compound produced by that the host compound is reacted with the guest compound in the presence of water and the product is dried to have the moisture content of 1% by weight or less can be advantageously used as a catalyst for curing powder paints, when taking into account the test results of curing the epoxy resin and the improvement of the pot life mentioned above.

EXAMPLE 15 TO 17

Preparation of a Molecular Compound According to Step (d)

A 1-L bench kneader (manufactured by Irie Syoukai Co., Ltd.) was heated to 70° C. 203.5 g (0.50 moles) of TEP (purity: 97.9%) was fed in the kneader. Water was added to it at a specified amount shown in Table 12 to mix with stirring for 3 minutes. Continuing stirring, 106.7 g (0.95 moles) of melted 2E4MZ (purity: 98.05%) was added all at once. The mixture was continuously stirred at the same temperature. A sample was taken at a fixed time shown in Table 12. The samples were subjected to catalytic activity evaluations by the same methods as those used in Example 6. Part of the sample taken after an hour was dried at 75° C. for 4.5 hours and subjected to the same catalytic activity evaluations. The results are together shown in Tables 12 and 13.

TABLE 12

| | | Example 15 | | Example 16 | | Example 17 | |
|---|---|---|---|---|---|---|---|
| | | Amount of water added (ml) | | | | | |
| | | 250 | | 200 | | 150 | |
| Sampling time (hours) | | Moisture (wt %) | Pot life (hours) | Moisture (wt %) | Pot life (hours) | Moisture (wt %) | Pot life (hours) |
| Before | 1.0 | 27.8 | | 17.4 | 20 | 9.2 | 9 |
| Dried | 2.5 | 1.23 | 159 | 0.21 | 96 | 0.16 | 34 |
| | 4.5 | 0.28 | 101 | 0.19 | 103 | 0.19 | 43 |
| After Dried | | 0.16 | 127 | 0.18 | 112 | 0.19 | 101 |

TABLE 13

| | | Example 15 | | | Example 16 | | Example 17 | |
|---|---|---|---|---|---|---|---|---|
| | | Amount of water added(ml) | | | | | | |
| | | 250 | | | 200 | | 150 | |
| | | Kneading time (hours) | | | | | | |
| | | 1.0 | 2.5 | 4.5 | 1.0 | 4.5 | 1.0 | 4.5 |
| Before dried | Moisture content (wt %) | | 1.2 | 0.28 | 17.4 | 0.19 | 9.2 | 0.19 |
| | Curing temperature | | 128-208 | 127-211 | 112-205 | 125-203 | 119-204 | 122-204 |
| | Top peak temp. (° C.) | | 154 | 154 | 151 | 153 | 152 | 152 |
| | Temp. to top peak (° C.) | | 26.1 | 27. | 38.9 | 28.0 | 32.6 | 29.6 |
| | Calorific value (mj/mg) | | 243.3 | 328.3 | 161.3 | 245.0 | 202.6 | 253.9 |
| After dried | Moisture content (wt %) | 0.16 | | | 0.18 | | 0.19 | |
| | Curing temperature | 125-204 | | | 124-204 | | 121-204 | |
| | Top peak temp. (° C.) | 155 | | | 153 | | 152 | |
| | Temp. to top peak (° C.) | 30.3 | | | 29.1 | | 30.3 | |
| | Calorific value (mj/mg) | 243.3 | | | 228.8 | | 224.3 | |

Table 12 shows the results of measurements of the pot lives of the epoxy resin. From the table, the samples (Example 15) taken from the product produced by adding 500 ml of water to a mole of the solid host compound greatly improved the pot lives of the paint, similar to the samples with the moisture content of 1% by weight or below and produced by adding different amounts of water, even if the molecular compound containing 1% by weight or more of moisture and obtained by that the host compound was reacted with the guest compound by stirring, mixing and kneading so that the moisture content was 1.2% by weight. The stability is considered to be improved because of the homogenized molecular compound produced by the reaction carried out in the presence of about 500 ml of water to a mole of the solid host compound. Table 13 shows the results of the test for curing the epoxy resin. It also reveals that the samples taken from the molecular compounds produced by adding 500 ml of water to a mole of the solid host compound resulted in higher curing temperatures, narrower temperature ranges to the top peaks and larger calorific values of the paint, same as those with the moisture content of 1% by weight or less and produced by adding different amounts of water. Therefore, curing of the epoxy resin started sharply and promptly. It is understood that the molecular compounds produced by that the host compound was reacted with the guest compound in the presence of about 500 ml of water to a mole of the solid host compound can be advantageously used as catalysts for curing powder paints, when taking into account the test results of curing the epoxy resin and the said improvement of the pot life.

EXAMPLE 18

Into a 500-ml beaker were placed 250 ml of water and 30 g (0.074 moles) of TEP described in Example 8 that was pulverized with a jet stream by an Ulmax pulverizer and had the same particle distribution, and heated to 50° C. 17.40 g (0.155 moles) of 2-ethyl-4-methylimidazole (2E4MZ) (produced by Shikoku Kasei Kogyo Co., Ltd.) was added all at once with stirring. The mixture was stirred with a motor at 500 rpm continuously for 3 hours, while keeping the temperature at 50° C. The solid was filtered, dried in an oven of 70° C. for 15 hours, and subjected to a powder X-ray diffraction measurement to confirm the crystallinity. The TG-DTA of the reaction product was measured for the thermal behavior. A decrease in weight was seen in the range of 194° C. to 221° C. The results are shown in Table 14.

Figure 5:
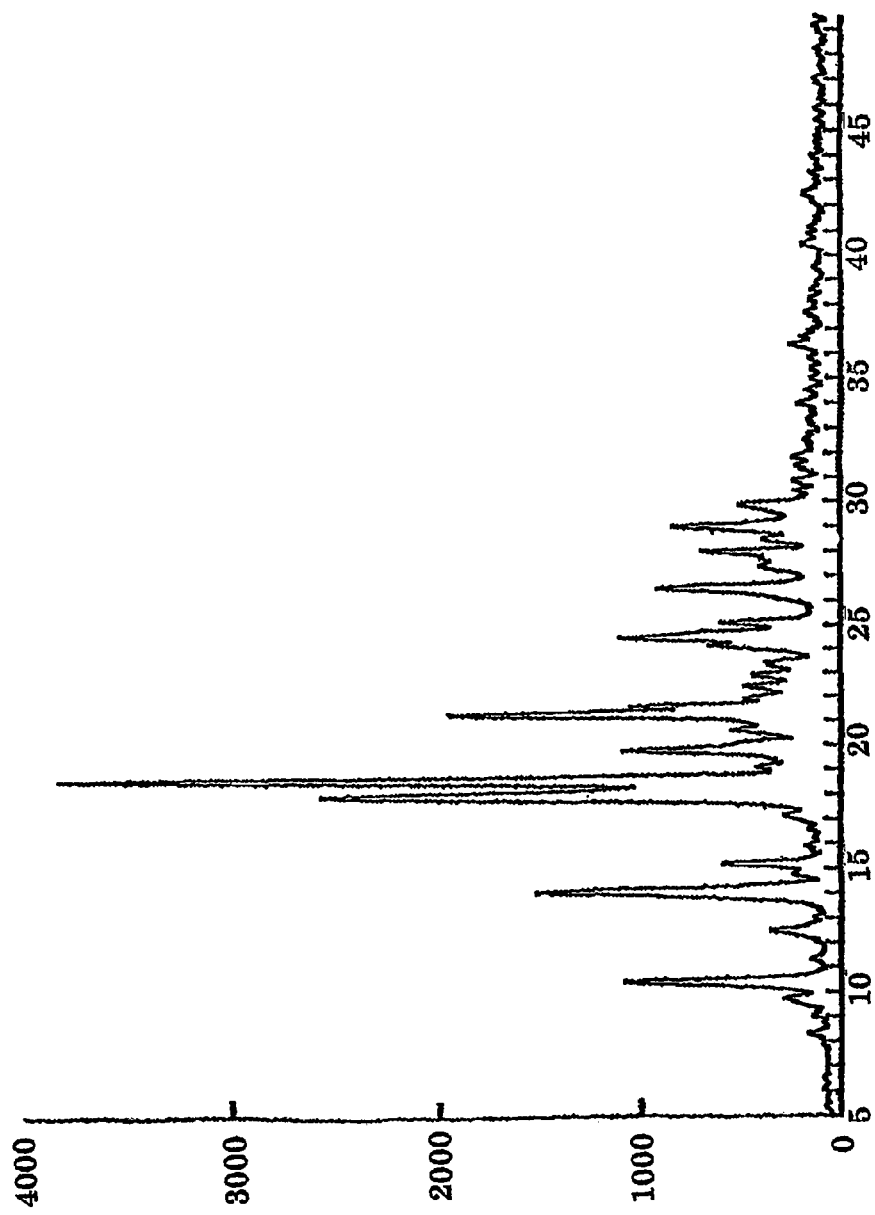
FIG. 5 shows a powder X-ray diffraction pattern of the molecular compound composing TEP and 2-ethyl-4-methylimidazole of Example 18 of the present invention.

The weight loss can be inferred to be due to the release of the guest compound. A rise in the release temperature was confirmed. An amount of 2E4MZ in the obtained solid was measured by HPLC and the moisture content by a Karl Fisher moisture titrator MKS-510 (manufactured by Kyoto Denshi Kogyo Co., Ltd.). The results are shown in Table 14. A powder X-ray diffraction pattern of the molecular compound produced in Example 18 is shown in FIG. 5.

EXAMPLES 19 TO 21

Example 18 was repeated except that the motor ran at 250 rpm instead of 500 rpm (Example 19). A molecular compound was produced in the same was as that in Example 18 except that the heating temperature was 30° C. instead of 50° C. (Example 20). Example 18 was repeated except that the reaction was carried out at 30° C. and 2E4MZ was added over 28 minutes (Example 21). The obtained solids were subjected to powder X-ray diffraction measurements, in the same way as that in the example, to confirm the crystallinity. TG-DTAs of the reaction products were measured for the thermal behaviors. Weight losses were seen at 197° C. (Example 19), at 191° C. (Example 20) and at 187° C. (Example 21). Rises in the release temperature ranges of the guest compound were confirmed. Amounts of 2E4MZ in the obtained solids were measured by HPLC and the moisture contents by a Karl Fisher moisture titrator MKS-510 (manufactured by Kyoto Denshi Kogyo Co., Ltd.). The results are shown in Table 14.

The molecular compounds produced in Examples 18 to 21 were subjected to catalytic activity evaluations by the same methods as those used before. The results are shown together in Table 14.

COMPARATIVE EXAMPLES 1 AND 2

Figure 6:
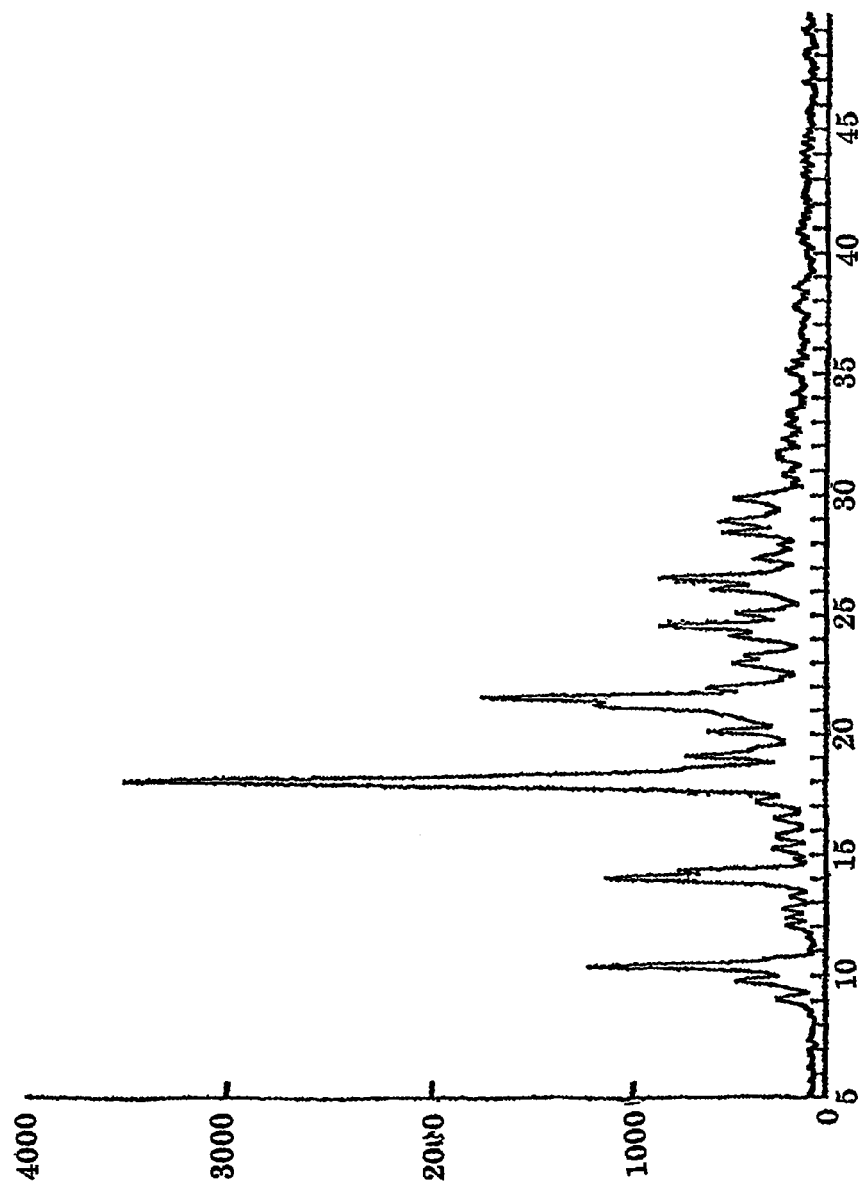
FIG. 6 shows a powder X-ray diffraction pattern of the molecular compound of Comparative Example 1.

Example 18 was repeated except that TEP that was not pulverized by an Ulmax pulverizer was used (Comparative Example 1). A reaction was carried out in the same way as that in Example 18 except that TEP used was not pulverized by an Ulmax pulverizer and the host and guest compounds were heated at 30° C. (Comparative Example 2). The obtained solids were subjected to powder X-ray diffraction measurements in the same way as that used in the example. TG-DTAs of the reaction products were measured for the thermal behaviors. The powder X-ray diffraction measurements revealed that the composition ratios of the host and guest compounds differed from those of the molecular compounds produced in the example. The TG-DTA measurements showed weight losses before reaching 187° C. (Comparative Example 1) and 181° C. (Comparative Example 2). The guest compound was released at lower temperatures. A powder X-ray diffraction pattern of the product of Comparative Example 1 is shown in FIG. 6

Amounts of 2E4MZ in the obtained compounds were measured by HPLC and the moisture contents by a Karl Fisher moisture titrator MKS-510 (manufactured by Kyoto Denshi Kogyo Co., Ltd.) in the same way as that used in the example. The results are shown in Table 14.

The obtained compounds were subjected to characteristics tests when they were applied as catalysts for curing epoxy resins, similarly to those produced in the examples. Pot lives and curing temperatures were measured by the same methods as those used in the example. The results are shown in Table 14.

TABLE 14

|  | Example 18 | Example 19 | Example 20 | Example 21 | Comparative Example 1 | Comparative Example 2 |
|---|---|---|---|---|---|---|
| TEP | Pulverized by Ulmax | Pulverized by Ulmax | Pulverized by Ulmax | Pulverized by Ulmax | Not pulverized | Not pulverized |
| 2E4MZ addition method | All at one | All at one | All at one | 28 minutes | All at one | All at one |
| Rotation (rpm) | 500 | 250 | 500 | 500 | 500 | 500 |
| Production temperature (° C.) | 50 | 50 | 30 | 30 | 50 | 30 |
| $1^{st}$ release temp. range (° C.) | 194.5-218.6 | 197.9-220.7 | 191.4-219.3 | 187.9-217.0 | 186.6-214.3 | 180.9-210.9 |
| $2^{nd}$ release temp. range (° C.) | 324.2-354.7 | 325.9-356.5 | 322.3-352.4 | 324.9-354.2 | 323.8-358.5 | 321.5-352.8 |
| 2E4MZ amount (wt %) | 33.1 | 32.4 | 33.5 | 31.9 | 27.2 | 25.9 |
| Moisture content (wt %) | 0.35 | 0.29 | 0.33 | 0.30 | 0.29 | 0.26 |
| Pot life (hours) | 234 | 185 | 106 | 126 | 139 | 60 |
| Curing temperature (° C.) | 130-201 | 128-205 | 121-206 | 128-209 | 123-206 | 121-199 |
| Top peak temperature (° C.) | 155.7 | 156.4 | 153.3 | 152.8 | 152.2 | 151.6 |

Table 14 shows the test results of measuring the pot lives of the epoxy resin. The samples taken from the products produced using TEP pulverized by the Ulmax pulverizer in the presence of the reaction solvent gave the paint longer pot lives, whether the stirring motor ran at a low rotation speed or the compounds were heated at 30° C. Therefore the stable molecular compound was obtained. Contrary to it, the sample taken from the molecular compound (Comparative Example 1) prepared using TEP that was not pulverized by an Ulmax pulverizer even if the reaction was carried out at 50° C. resulted in a shorter pot life of the paint, and the sample (Comparative Example 2) prepared using TEP that was not pulverized by an Ulmax pulverizer and the reaction was carried out at 30° C. resulted in an extremely shorter pot life of the paint. It was recognized both of the molecular compounds were less stable. In addition, with the samples of the molecular compounds of Examples 18 to 21, high curing temperatures and high top peak temperatures of the paint were attained. The molecular compounds were improved in stability. It is understood that the molecular compounds can be advantageously used as catalysts for curing powder paints.

According to the methods of the present invention, molecular compounds can be mass-produced at an industrial scale without using solvents. The obtained molecular compound not only can be made a homogeneous product in a short time but also is improved in stability, differing from that produced by a solvent method.

The methods of the present invention for producing molecular compounds produce molecular compounds with improved stability, even if a poor solvent is used. Therefore, the molecular compounds can be advantageously used as catalysts for curing thermosetting resin paints and the like.

The invention claimed is:

1. A method for producing a clathrate having improved stability which comprises mixing and/or kneading a solid host compound with a solid or liquid guest compound, the solid host compound being selected from tetrakisphenols, and the solid or liquid guest compound being selected from imidazoles, and comprising at least one of the following steps: (a) holding the clathrate at a temperature of between about 50° C. and 170° C. for 1 to 6 weeks; (c) pulverizing the solid host compound by a jet stream prior to mixing and/or kneading; or (d) adding a poor solvent in an amount of between 200 ml and 1000 ml to a mole of the solid host compound prior to mixing and/or kneading, the poor solvent being a solvent that dissolves 1 g/100 ml or less of the solid host compound and the solid or liquid guest compound at room temperature.

2. A method according to claim 1, wherein the solid host compound is pulverized to an average particle size of 1.6 μm or smaller in Step (c).

3. A method according to claim 1, wherein the solid host compound is pulverized to a particle size of 4.0 μm or smaller in Step (c).

4. A method according to claim 1 wherein 80% by weight or more of the solid host compound is pulverized to 2.0 μm or smaller in particle size in Step (c).

5. A method according to one of claim 1; wherein the poor solvent is added at an amount of 20 to 200% by weight to the total weight of the solid host compound and the solid or liquid guest compound prior to mixing and/or kneading in Step (d).

6. A method according to claim 1 wherein the poor solvent is added, and the solid host compound is mixed and/or kneaded with the solid or liquid guest compound while heating so that the content of the solvent becomes 1% by weight or below in Step (d).

7. A method according to claim 1 (wherein the poor solvent is added to the host and guest compounds to mix and/or knead, followed by drying the product so that the content of the solvent is 1% by weight or less in Step (d).

8. A method according to claim 1 wherein the poor solvent used in Step (d) is water.

9. A method according to claim 1 wherein the solid host compound is mixed with a required amount of the solid guest compound or with a necessary amount of the liquid guest compound all at once.

10. A method for producing a clathrate, comprising: pulverizing a solid host compound to an average particle size of 1.6 μm or smaller, the solid host compound being selected from tetrakisphenols; and dispersing the pulverized solid host compound and a solid or liquid guest compound in a poor solvent, the solid or liquid guest compound being selected from imidazoles, the solid host compound being from 10 to 50% by weight in concentration, and the poor solvent being a solvent that dissolves 1 g/100 ml or less of the solid host compound and the solid or liquid guest compound at room temperature.

11. A method for producing a clathrate, comprising: pulverizing a solid host compound to a particle size of 4.0 μm or smaller, the solid host compound being selected from tetrakisphenols; and dispersing the pulverized solid host compound and a solid or liquid guest compound in a poor solvent, the solid or liquid guest compound being selected from imidazoles, the solid host compound being from 10 to 50% by weight in concentration, and the poor solvent being a solvent that dissolves 1 g/100 ml or less of the solid host compound and the solid or liquid guest compound at room temperature.

12. A method for producing a clathrate, comprising: pulverizing 80% by weight or more of a solid host compound to 2.0 μm or smaller in particle size, the solid host compound being selected from tetrakisphenols; and dispersing the pulverized host compound and a solid or liquid guest compound in a poor solvent, the solid or liquid guest compound being selected from imidazoles, the solid host compound being from 10 to 50% by weight in concentration, the poor solvent being a solvent that dissolves 1 g/100 ml or less of the solid host compound and the solid or liquid guest compound at room temperature.

13. A method according to claim 10 in which the solid host compound is preferably pulverized by a jet stream.

14. A method according to claim 11 in which the solid host compound is preferably pulverized by a jet stream.

15. A method according to claim 12 in which the solid host compound is preferably pulverized by a jet stream.

16. A method for producing a molecular compound according to claim 10 in which the poor solvent is water.

17. A method for producing a molecular compound according to claim 11 in which the poor solvent is water.

18. A method for producing a molecular compound according to claim 12 in which the poor solvent is water.

19. A method according to claim 1, wherein the solid host compound is 1,1,2,2-tetrakis(4-hydroxyphenyl) ethane.

20. A method according to claim 10, wherein the solid host compound is 1,1,2,2-tetrakis(4-hydroxyphenyl) ethane.

21. A method according to claim 11, wherein the solid host compound is 1,1,2,2-tetrakis(4-hydroxyphenyl) ethane.

22. A method according to claim 1, wherein the solid or liquid guest compound is 2-ethyl-4-methylimidazole.

23. A method according to claim 10, wherein the solid or liquid guest compound is 2-ethyl-4-methylimidazole.

24. A method according to claim 11, wherein the solid or liquid guest compound is 2-ethyl-4-methylimidazole.

25. A method according to claim 12, wherein the solid or liquid guest compound is 2-ethyl-4-methylimidazole.

* * * * *